US011229649B2

(12) United States Patent
Huston et al.

(10) Patent No.: US 11,229,649 B2
(45) Date of Patent: *Jan. 25, 2022

(54) METHODS FOR TREATING CRYPTOSPORIDIOSIS USING TRIAZOLOPYRIDAZINES

(71) Applicant: University of Vermont and State Agricultural College, Burlington, VT (US)

(72) Inventors: Christopher D. Huston, Burlington, VT (US); Kovi Bessoff, Houston, TX (US); Rajiv Satish Jumani, Colchester, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,487

(22) Filed: Jul. 29, 2019

(65) Prior Publication Data

US 2019/0343837 A1    Nov. 14, 2019

Related U.S. Application Data

(63) Continuation of application No. 15/563,325, filed as application No. PCT/US2016/025284 on Mar. 31, 2016, now Pat. No. 10,363,254.

(Continued)

(51) Int. Cl.
*A61K 31/495* (2006.01)
*A61K 31/5025* (2006.01)
(Continued)

(52) U.S. Cl.
CPC ........ *A61K 31/5025* (2013.01); *A61K 9/0019* (2013.01); *A61K 9/0053* (2013.01);
(Continued)

(58) Field of Classification Search
CPC ........................ A61K 31/5025; C07D 487/04
(Continued)

(56) References Cited

U.S. PATENT DOCUMENTS

2006/0165778 A1   7/2006   Hassan et al.
2006/0286109 A1   12/2006   Audonnet et al.
(Continued)

FOREIGN PATENT DOCUMENTS

WO   2007064797 A2   6/2007
WO   2013040527 A1   3/2013
WO   2013082469 A2   6/2013

OTHER PUBLICATIONS

PubChem CID 1476861 (Year: 2005).*
(Continued)

*Primary Examiner* — Shengjun Wang
(74) *Attorney, Agent, or Firm* — Hodgson Russ LLP

(57) ABSTRACT

Methods for treating or prophylaxis of a *cryptosporidium* infection using compositions comprising a structure disclosed herein. Also provided are pharmaceutical compositions and kits for alleviating the symptoms of, for treating, or for preventing the occurrence of *cryptosporidium* infection. The kits comprise one or more compounds having a structure disclosed herein, such as in an oral composition, and instructions for use, storage, and the like.

4 Claims, 14 Drawing Sheets

For each set of data for a day, the bars from left to right are: DMSO, MMV665917, MMV675977, and MMV672987

Related U.S. Application Data

(60) Provisional application No. 62/140,762, filed on Mar. 31, 2015.

(51) Int. Cl.
*A61K 31/551* (2006.01)
*A61K 9/00* (2006.01)
*A61K 47/10* (2017.01)
*A61K 9/14* (2006.01)
*A61K 9/50* (2006.01)

(52) U.S. Cl.
CPC ............ *A61K 9/146* (2013.01); *A61K 9/5021* (2013.01); *A61K 31/551* (2013.01); *A61K 47/10* (2013.01); *Y02A 50/30* (2018.01)

(58) Field of Classification Search
USPC .......................................... 514/248; 544/236
See application file for complete search history.

(56) References Cited

U.S. PATENT DOCUMENTS

| | | |
|---|---|---|
| 2008/0027044 A1 | 1/2008 | Lewis et al. |
| 2010/0016279 A1* | 1/2010 | Bradbury ............ C07D 471/04 514/210.21 |
| 2010/0267699 A1 | 10/2010 | Bradbury et al. |

OTHER PUBLICATIONS

PubChem CID 20878040 (Year: 2007).*
PubChem CID 45535957 (Year: 2010).*
PubChem CID 45502054 (Year: 2010).*
PubChem CID 44070736 (Year: 2009).*
PubChem CID 5308707 (Year: 2005).*
STN RN 904576-18-7 Aug. 25, 2006.
STN RN 1040640-07-0 Aug. 13, 2008.
STN RN 1058444-51-1 Oct. 8, 2008.
STN RN 904576-65-4 Aug. 25, 2006.

Bradbury et al., Small-molecule androgen receptor downregulators as an approach to treatment of advanced prostrate cancer, Bioorganic and Medicinal Chemistry Letters, vol. 21, No. 18, pp. 5442-5445 Jul. 2, 2011.

Aldrich et al., MAOS protocol for the general synthesis and lead optimization of 3,6-disubstituted-[1,2,4]triazolo[4,3-b]pyridazines, Tetrahedron Letters, vol. 50, No. 2, pp. 212-215 Jan. 14, 2009.

Katrusiak et al., Triazolo- and tetrazolopyridazine derivatives and their hypotension and heart rate activity, Acta Poloniae Pharmaceutica, vol. 58, No. 3, pp. 217-223 May 2001.

Zhang et al., Discovery and characterization of novel small-molecule agonists of G protein-coupled receptor 119, vol. 12, No. 4, pp. 540-548 Apr. 2014.

Loddick et al., AZD3514: A Small Molecule That Modulates Androgen Receptor Signalling and Function In Vitro and In Vivo, Molecular Cancer Therapeutics, vol. 12, No. 9, pp. 1715-1727 Sep. 2013.

Bucur et al., A novel capase 8 selective small molecule potentiates TRAIL-induced cell death, Scientific Reports, vol. 5, No. 1, pp. 1-12 May 11, 2015.

Lendner et al., A novel CDPK1 inhibitor-a potential treatment for cryptosporidiosis in calves?, Parasitology Research, vol. 114, No. 1, pp. 335-336 Nov. 15, 2014.

Graczyk et al., Novel and promising compounds to treat Cryptosporidium parvum infections, Parasitology Research, vol. 109, No. 3, pp. 591-594 Feb. 23, 2011.

Rossignol et al., Cryptosporidium and Giardia: Treatment options and prospects for new drugs, Experimental Parasitology, vol. 124, No. 1, pp. 45-53 Jan. 1, 2010.

Watari et al., Feeding Activated Charcoal from Bark Containing Wood Vinegar Liquid (Nekka-Rich) Is Effective as Treatment for Cryptosporidosis in Calives, Journal of Dairy Science, vol. 91, No. 4, pp. 1458-1463 Apr. 1, 2008.

Benbow et al., Synthesis and evaluation of dinitroanilines for treatment of cryptosporidiosis, CAPLUS 1998.

Louis et al., Treatment of Cyptosporidiosis with Oral Bovine Transfer Factor, Clinical Immunology and Immunopathology, vol. 44, No. 3, pp. 329-334 1987.

* cited by examiner

MMV011944
EC50 = 3.5 μM

MMV665917
EC50 = 3.8 μM

MMV000760
EC50 = 0.26 μM

MMV665852
EC50 = 6.4 μM

MMV665909
EC50 = 3.1 μM

MMV006753
EC50 = 0.11 μM

For each set of data for a day, the bars from left to right are: DMSO, MMV665917, MMV675977, and MMV672987

Figure 4

| ALogP | Mouse PK Data (PO) MMV665917 ||||||||
|---|---|---|---|---|---|---|---|
| | Administered dose (μmol/kg) | $C_{max}$ (μmol/L) | $T_{max}$ (h) | $T_{1/2}$ (h) | $T_{last}$ (h) | $AUC_{0-last}$ (h*μmol/L) | $AUC_{0-inf}$ (h*μmol/L) | Kinetic Solubility pH 7.4 (μM) |
| 1.693 | 153 | 13.8 ± 2.29 | 6 | NR | 9 | 89.9 ± 10.6 | NR | 18.84 |

| Mouse PK Data (PO) MMV665917 |||||
|---|---|---|---|---|
| | $T_{1/2}$ (min) | $CL_{int}$ (mL/min/kg) | $CL$ (μL/min/mg) | $CL_h$ (mL/min/kg) |
| Mouse | >289.1 | <28.5 | | |
| | >145.0 | <75.6 | <19.1 | 41.1 |
| Human | 252.6 | 9.9 | | |
| | >145.0 | <18.9 | <19.1 | <9.9 |

| % Remaining after Incubation (60 min) ||
|---|---|
| Human Plasma | 96.3 |
| CD-1 Mouse Plasma | 97.5 |

| CD-1 Mouse Liver Microsome ||
|---|---|
| Fraction Unbound | <0.01 |
| Fraction Bound | >0.99 |
| % Recovery | 78.4 |

Figure 4 (continued)

|  | Human Plasma | CD-1 Mouse Plasma |
|---|---|---|
| % Unbound | 11.2 | 16.7 |
| % Bound | 88.8 | 83.3 |
| Recovery | 88.4 | 82.8 |

| Cell Line | Inhibition % of DMSO control | IC$_{50}$ (µM) |
|---|---|---|
| 1A2 | 26.5 | 27.8 |
| 2C9 | 32.6 | 20.7 |
| 2C19 | 48.5 | 10.6 |
| 2D6 | 62.9 | 5.9 |
| 3A4-M | 35.6 | 18.1 |
| 3A4-T | 36.0 | 17.8 |

| hERG % inhibition (1 µM) | SEM | Count | hERG % inhibition (11 µM) | SEM | Count | hERG activity level |
|---|---|---|---|---|---|---|
| 0 | 4 | 10 | 58 | 5 | 10 | Active |

Figure 4 (continued)

| | Species | Male Sprague Dawley rat (269 – 273 g) | |
|---|---|---|---|
| STUDY DESIGN | Dose route | IV | PO |
| | Target Dose | 1 mg/kg (n=2) | 5 mg/kg (n=2) |
| | Dosing details | 10 min constant rate infusion 1 mL per rat | Via gavage needle 10 mL/kg |
| | Plasma collection | Pre, 5, 10 min (during infusion); Post-infusion: 5, 20 min, 1, 2.5, 5, 10, 16, 2 4h | Pre, 15, 30 min, 1, 2.5, 4, 5, 10, 16 24 h |
| | Urine collection | Pooled (24 h) | Pooled (24 h) |
| FORMULATION | Vehicle | Aqueous vehicle containing 40% (v/v) propylene glycol and 10% (v/v) ethanol | HPMC-SV which is an aqueous vehicle containing 0.5% (w/v) hydroxypropyl methylcellulose, 0.5% (v/v) benzyl alcohol and 0.4% (v/v) Tween 80 |
| | Appearance | Clear, colourless solution | Fine, milky white, uniform suspension |
| | Target Concentration | 0.28 mg/mL | 0.50 mg/mL |

Figure 4 (continued)

| Instrument | Waters Micromass Quattro Premier coupled to a Waters Acquity UPLC |
|---|---|
| Detection | Positive electrospray ionisation multiple-reaction monitoring mode |
| Column | Supelco Ascentis Express RP Amide column (50 x 2.1 mm, 2.7 μm) |
| LC conditions | Gradient cycle time: 4 min; Injection vol: 3 μL; Flow rate: 0.4 mL/min |
| Mobile phase | ACN-Water gradient with 0.05% formic acid |
| Extraction | Protein precipitation for plasma using acetonitrile (2-fold volume ratio) |

| Analyte | $t_R$ (min) | Transition (m/z) | Cone voltage (V) | CID (V) |
|---|---|---|---|---|
| MMV665917 | 1.93 | 358.21 > 205.21 | 40 | 20 |
| Diazepam (internal standard) | 2.20 | 285.20 > 154.10 | 40 | 25 |

| Incubation Time (min) | % MMV665917 remaining * | |
|---|---|---|
| | Plasma | Whole Blood # |
| 2 | 100 | 100 |
| 60 | 99.7 | 99.9 |
| 120 | 95.0 | 99.9 |
| 240 | 95.1 | 105 |

* Calculated relative to the 2 minute sample.
Based on assay of the plasma fraction.

| Parameter | IV administration | | Mean | Oral administration | | Mean |
|---|---|---|---|---|---|---|
| | E_2813 | F_2813 | | G_2813 | H_2813 | |
| Measured dose (mg/kg) | 0.9 | 0.9 | 0.9 | 3.2 | 3.3 | 3.3 |
| Apparent $t_{1/2}$ (h) | 3.0 | 3.5 | 3.2 | 3.0 | 3.7 | 3.4 |
| Plasma $CL_{total}$ (mL/min/kg) | 5.7 | 5.2 | 5.5 | --- | --- | --- |
| Plasma $V_{ss}$ (L/kg) | 1.3 | 1.1 | 1.2 | --- | --- | --- |
| B/P ratio | --- | --- | 1.1 | --- | --- | --- |
| Blood $CL_{total}$ (mL/min/kg) | 5.2 | 4.8 | 5.0 | --- | --- | --- |
| Blood $V_{ss}$ (L/kg) | 1.2 | 1.0 | 1.1 | --- | --- | --- |
| % Dose in urine [a] | 26.0 | 24.8 | 25.4 | 8.8 | 6.7 | 7.8 |
| $C_{max}$ (μM) | --- | --- | --- | 0.9 | 1.5 | 1.2 |
| $T_{max}$ (h) | --- | --- | --- | 5 | 5 | 5 |
| $AUC_{0-inf}$ (h*μM) | 7.3 | 8.0 | 7.7 | 6.6 | 12.3 | 9.5 |
| BA (%) | --- | --- | --- | 24 | 43 | 34 |

[a] Unchanged MMV665917 present in pooled urine (collected over 0-24 h).

Figure 4 (continued)

| Compound | Matrix | QC Data | | | Calibration Data | | |
|---|---|---|---|---|---|---|---|
| | | QC ^ (ng/mL) | Accuracy (% bias)* | Precision (%RSD) | Range ^ (ng/mL) | $R^2$ | LLQ # (ng/mL) |
| MMV665917 | Plasma | 50 (n=6) | -0.1 | 5.4 | 5 - 10,000 | 0.9999 | 5.0 |
| | | 500 (n=6) | -0.9 | 7.8 | | | |
| | Solvent | 500 (n=4) | -0.8 | 2.2 | 2.5 - 5,000 | 0.9991 | 2.5 |

* Acceptance criteria for batch analysis: at least 67% of the QC samples lie within ±15% of nominal values (FDA Guidance for Industry: Bioanalytical Method Validationn, May 2001).

Lower limit of quantification (LLQ) is defined by the lowest acceptable calibration standard for which the back calculated concentration lies within ±20% of the nominal concentration.

^ Blank plasma (for the analysis of plasma samples) or 50% acetonitrile/water (for the analysis of formulation aliquots and urine) was used for preparation of the calibration standards and QC samples. Data were fitted to a linear quadratic equation as appropriate.

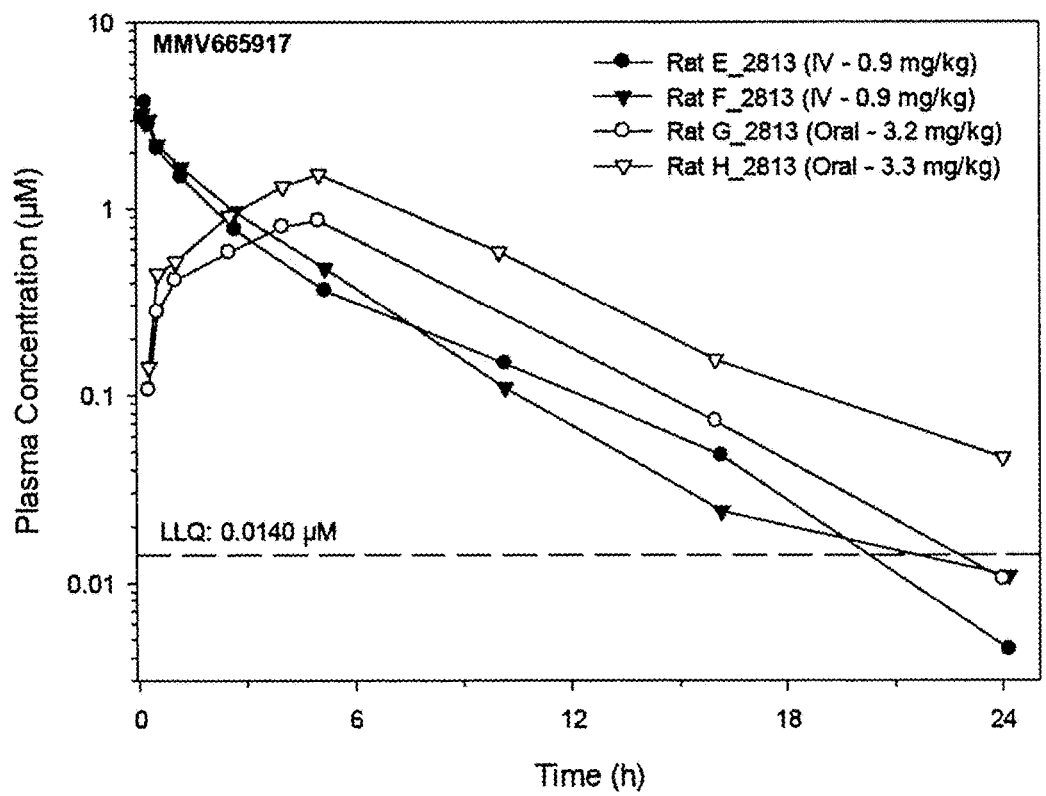

Figure 4 (continued)

| IV Administration | | | |
|---|---|---|---|
| | Plasma concentration (ng/mL) | | |
| Time (h) [a] | Rat E_2813 (0.9 mg/kg) | Rat F_2813 (0.9 mg/kg) | Mean |
| Pre | ND | ND | --- |
| 0.08 | 1098.9 | 1162.6 | 1130.8 |
| 0.17 | 1334.1 | 1038.5 | 1186.3 |
| 0.25 | 1007.8 | 1075.0 | 1041.4 |
| 0.5 | 752.0 | 792.8 | 772.4 |
| 1.17 | 528.0 | 595.3 | 561.7 |
| 2.67 | 275.5 | 344.2 | 309.9 |
| 5.17 | 129.5 | 171.5 | 150.5 |
| 10.17 | 52.7 | 39.0 | 45.9 |
| 16.17 | 16.9 | 8.6 | 12.8 |
| 24.17 | 1.6 [b] | 3.9 [b] | 2.7 |
| Oral Administration | | | |
| | Plasma concentration (ng/mL) | | |
| Time (h) | Rat G_2813 (3.2 mg/kg) | Rat H_2813 (3.3 mg/kg) | Mean |
| Pre | ND | ND | --- |
| 0.25 | 38.1 | 50.4 | 44.2 |
| 0.5 | 99.6 | 160.0 | 129.8 |
| 1 | 147.8 | 186.0 | 166.9 |
| 2.5 | 208.8 | 326.9 | 267.8 |
| 4 | 286.1 | 469.4 | 377.7 |
| 5 | 307.5 | 545.4 | 426.4 |
| 10 | 2658.5 [c] | 209.6 | 209.6 |
| 16 | 25.8 | 55.0 | 40.4 |
| 24 | 3.7 [b] | 16.5 | 10.1 |

[a] Relative to the start of the infusion.
[b] Value is below the analytical LLQ (5 ng/mL) and is an approximation only.
[c] Value was excluded as it was not consistent with other data in profile.

Mean MMV665917 Plasma Concentrations (ng/mL) Following IV or PO Administration to Mice, Rats and Calves

- Linearity within rodent species as predicted by 50 mg/kg PO simulation in rat
- Increased plasma exposure in calves, higher bioavailibility in calves than in rodents (rat F%: 34%) predicted Actual and Simulated MMV665917 Plasma Concentrations (uM) Following PO Administration to Mice and Calves

*A single 55 mg/kg mouse PO dose of MMV665917 was used to simulate the 30 and 60 mg/kg PO BID plasma concentrations (simulated dosing intervals were 12 hr apart). The simulated 60 mg/kb BID doses would have achieved 3x EC90 concentrations observed in the parasite persistence assay.*

METHODS FOR TREATING CRYPTOSPORIDIOSIS USING TRIAZOLOPYRIDAZINES

CROSS-REFERENCE TO RELATED APPLICATIONS

This application is a continuation application of U.S. patent application Ser. No. 15/563,325, filed Sep. 29, 2017, which is a National Stage Application of International Application No. PCT/US16/25284, filed Mar. 31, 2016, which claims priority to U.S. Provisional Patent Application No. 62/140,762, filed Mar. 31, 2015, the disclosures of which are incorporated herein by reference.

FIELD OF THE INVENTION

The present disclosure generally relates to treatment of cryptosporidiosis. More particularly, the present disclosure relates to triazolopyridazine compounds for treating parasites (e.g., cryptosporidiosis).

BACKGROUND OF THE DISCLOSURE

The apicomplexan parasites *Cryptosporidium parvum* and *Cryptosporidium hominis* are major etiologic agents of cryptosporidiosis in humans. Infection is typically self-limited in immunocompetent adults, but it can lead to chronic and fulminant disease in immunocompromised patients, as well as malnutrition and stunting in children. Nitazoxanide is the current standard of care for cryptosporidiosis, but the drug only exhibits partial efficacy in children and is no more effective than placebo in AIDS patients. Unfortunately, the development of novel therapeutics for cryptosporidiosis has proven to be extremely difficult as a result of the financial obstacles that plague drug discovery for diseases that disproportionately affect the developing world, as well as technical limitations associated with the laboratory study of *Cryptosporidium* parasites.

While cryptosporidiosis is a significant cause of self-limited diarrhea in immunocompetent individuals who may be exposed to parasites through contaminated municipal and recreational water supplies or through occupational exposures, the burden of cryptosporidiosis is even more substantial in immunocompromised and pediatric populations. Immunodeficient individuals, including patients maintained on immunosuppressive regimens following organ transplantation and AIDS patients, in particular, risk developing chronic, fulminant, and sometimes fatal disease (especially when CD-4$^+$ T-cell counts drop below 50 cells/mm$^3$). Diarrhea is also a leading cause of death in children under 5 years of age, and the recent Global Enteric Multicenter Study (GEMS) identified *Cryptosporidium* as a major cause of life-threatening diarrhea during the first two years of life. Moreover, cryptosporidiosis has been associated with malnutrition and persistent deficits in development in this population.

SUMMARY OF THE DISCLOSURE

The present disclosure relates to methods for treating or prophylaxis of a *cryptosporidium* infection. For example, the method comprises administering to an individual diagnosed with or suspected of having a *cryptosporidium* infection or at risk of having *cryptosporidium* infection, a composition comprising a therapeutically effective or a prophylactically effective amount of a compound disclosed herein. The present disclosure also provides pharmaceutical compositions for alleviating the symptoms of, for treating, or for preventing the occurrence of *cryptosporidium* infection. In one embodiment, the pharmaceutical compositions are suitable for oral administration. The present disclosure also provides kits for alleviating the symptoms of, for treating, or for preventing the occurrence of *cryptosporidium* infection. The kits comprise one or more compounds of the present disclosure (such as in an oral composition) and instructions for use, storage and the like.

BRIEF DESCRIPTION OF THE FIGURES

FIG. 4 provides data of the pertinent physicochemical, pharmacokinetic, and oral bioavailability data for MMV665917. Additionally, hERG inhibition studies with MMV665917 are also included.

DETAILED DESCRIPTION OF THE DISCLOSURE

Figure 1:
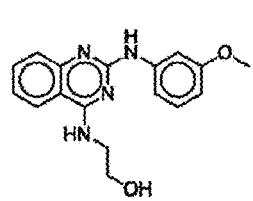
FIG. 1 shows structures and in vitro $EC_{50}$ values for inhibition of *C. parvum* development in HCT-8 cells for examples of compounds of the present disclosure.
Figure 1:
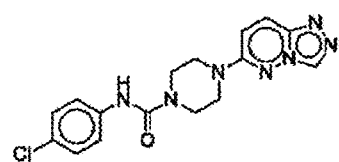
Figure 1:
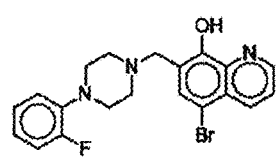
Figure 1:
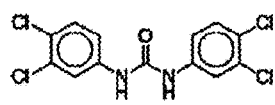
Figure 1:
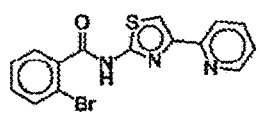
Figure 1:
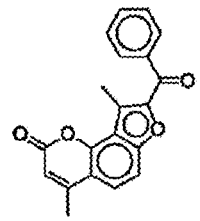

In an aspect, the present disclosure provides a method for treating a *cryptosporidium* infection or a method for prophylaxis comprising administering to an individual a therapeutically effective amount of a compound having a [1,2,4] triazolo[4,3-b]pyridazine (henceforth referred to as "triazolopyridazine") scaffold.

As used herein, the term "alkyl group," unless otherwise stated, refers to branched or unbranched hydrocarbons. Examples of such alkyl groups include methyl groups, ethyl groups, propyl groups, butyl groups, iso-propyl groups, sec-butyl, tert-butyl groups, and the like. For example, the alkyl group is a $C_1$ to $C_9$ alkyl group, including all integer numbers of carbons and ranges of numbers of carbons therebetween. Alkyl groups can be substituted with various other functional groups. The alkyl groups may be substituted with groups such as, for example, amines (acyclic and cyclic), alcohol groups, ether groups, and halogen atoms.

As used herein, unless otherwise indicated, alkoxy means where $R^a$ is a linear, branched or cyclic $C_1$-$C_6$ alkyl group, including all integer numbers of carbons and ranges of numbers of carbons therebetween. For example, suitable alkoxy groups include methoxy, ethoxy, propoxy, iso-propoxy, butoxy, sec-butoxy, tert-butoxy, and hexoxy groups. Additionally, alkyl substituents can be substituted with various other functional groups, e.g. functional groups disclosed herein.

As used herein, unless otherwise indicated, amino means where each $R^b$ is selected independently from the group consisting of hydrogen atom, substituted or unsubstituted $C_1$-$C_{10}$ alkyl, including all integer numbers of carbons and ranges of numbers of carbons therebetween, substituted or unsubstituted phenyl, substituted or unsubstituted heteroaryl, substituted carbonyl, substituted sulfonyl, haloalkyl, and substituted or unsubstituted benzyl groups.

As used herein, unless otherwise indicated, benzyl group means where $R^c$ is a substituent on the phenyl ring and n is from 0 to 5. The substituents can be the same or different. For example, the substituents on the benzyl group include substituted or unsubstituted alkyl, —$NH_2$, phenyl, haloalkyl (e.g., —$CF_3$), halo (e.g., —F, —Cl, —Br, —I), alkoxy (e.g., —OMe), and —OH groups.

As used herein, the term "cycloalkyl" refers to a cyclic hydrocarbon group, e.g., cyclopropyl, cyclobutyl, cyclohexyl, and cyclopentyl groups. Cycloalkyl groups can be saturated or partially unsaturated ring systems optionally substituted with, for example, one to three groups. Each group is independently selected from the group consisting of alkyl, —$NH_2$, oxo (=O), phenyl, haloalkyl (e.g., —$CF_3$), halo (e.g., —F, —Cl, —Br, —I), alkoxy, and —OH groups. Additionally, alkyl substituents may be substituted with various other functional groups.

As used herein, unless otherwise indicated, halogen means fluorine, chlorine, bromine, and iodine, and halo means fluoro, chloro, bromo, and iodo.

As used herein, the term "heteroaryl" refers to a monocyclic or bicyclic ring system comprising one or two aromatic rings and containing at least one nitrogen or oxygen atom in an aromatic ring. Unless otherwise indicated, a heteroaryl group can be unsubstituted or substituted with one or more, and in particular one or two, substituents selected from the group consisting of, for example, haloalkyl (e.g., —$CF_3$), halo (e.g., —F, —Cl, —Br, —I), alkyl, alkoxy, amino, —$CO_2H$, —$CO_2$alkyl, aryl, and heteroaryl groups. Examples of heteroaryl groups include, benzofuranyl, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl groups.

As used herein, unless otherwise indicated, —OPh (phenoxy) means

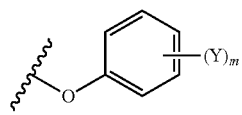

where each Y is independently selected from the group consisting of F, Cl, Br, and I and m can be 0, 1 or 2.

As used herein, unless otherwise indicated, phenyl group means

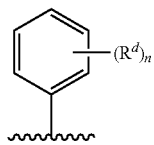

where each $R^d$ is an independent substituent on the phenyl group and n is from 0 to 5. The substituents at different occurrences can be the same or different. For example, the substituents on the phenyl group include substituted or unsubstituted $C_1$-$C_6$ alkyl, including all integer numbers of carbons and ranges of numbers of carbons therebetween, substituted or unsubstituted amino, haloalkyl (e.g., —$CF_3$), halo (e.g., —F, —Cl, —Br, —I), substituted or unsubstituted alkoxy (e.g., —OMe), and sulfonyl group. In certain instances, two adjacent R groups can be connected through to form a dioxolyl group.

As used herein, unless otherwise indicated, sulfonyl group means

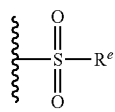

where $R^e$ can be a linear, branched or cyclic alkyl group, or amino group of the structure

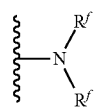

where each $R^f$ is independently selected from a hydrogen atom, linear, branched and cyclic alkyl group. They may also combine to form

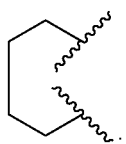 [SMILES: *CCCC*]

In an aspect, the present disclosure provides a methods for treating an individual diagnosed with or suspected of having a *cryptosporidium* infection. Compounds of the present disclosure can be used in the methods.

In an embodiment, a method for treating an individual diagnosed with or suspected of having a *cryptosporidium* infection comprises administering to the individual a therapeutically effective amount of a compound having a composition comprising the following structure:

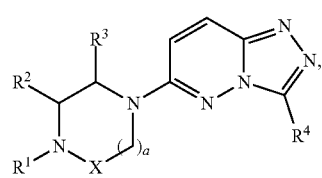

(I)

where $R^1$ is selected from the group consisting of hydrogen atom, substituted or unsubstituted $C_1$-$C_8$ alkyl group, sulfonyl group having the structure: —$S(O)_2R$, and carbonyl containing group having the structure: —$C(O)R$, —$C(O)_2R$, or —$C(O)N(R)_2$, where R is independently selected from the group consisting of hydrogen atom, substituted or unsubstituted $C_1$-$C_9$ alkyl group, including all integer numbers of carbons and ranges of numbers of carbons therebetween, substituted or unsubstituted heteroaryl group, substituted or unsubstituted alkoxy group, substituted or unsubstituted amino group, substituted or unsubstituted phenyl group, substituted or unsubstituted benzyl group, substituted or unsubstituted heteroaryl group, and substituted or unsubstituted —$CH_2$-heteroaryl group comprising 1 to 4 O and/or N atoms; $R^2$ is a hydrogen atom, or it may also combine with $R^1$ to form

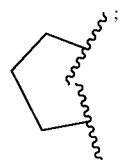 [SMILES: *CCC*]

$R^3$ is a hydrogen atom, or a substituted or unsubstituted $C_1$ to $C_9$ alkyl group, including all integer numbers of carbons and ranges of numbers of carbons therebetween $R^4$ is selected from the group consisting of hydrogen atom, substituted or unsubstituted $C_1$ to $C_9$ alkyl group, including all integer numbers of carbons and ranges of numbers of carbons therebetween, $C_3$-$C_6$ cycloalkyl group, substituted or unsubstituted $C_1$-$C_6$ haloalkyl group, including trifluoromethyl group, and phenyl derivative having the structure:

where Y is independently selected from the group consisting of F, Cl, Br, and I, and n can be 0, 1, 2, 3, 4, or 5. X is $CH_2$ or C=O; and a is 1 or 2.

In an embodiment, the compound has the following structure:

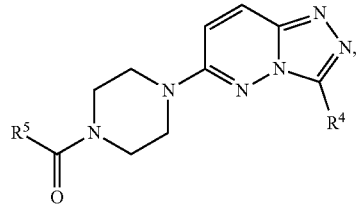
(II)

where $R^5$ is selected from the group consisting of substituted or unsubstituted alkyl group, substituted or unsubstituted $C_3$ to $C_6$ cycloalkyl group, substituted or unsubstituted benzyl group, substituted or unsubstituted amino group, substituted or unsubstituted phenyl group, substituted or unsubstituted alkoxy group, substituted or unsubstituted alkylheterocyclic group, substituted or unsubstituted phenoxy group, and substituted or unsubstituted aniline group. In various embodiments $R^5$ is selected from the group consisting of:

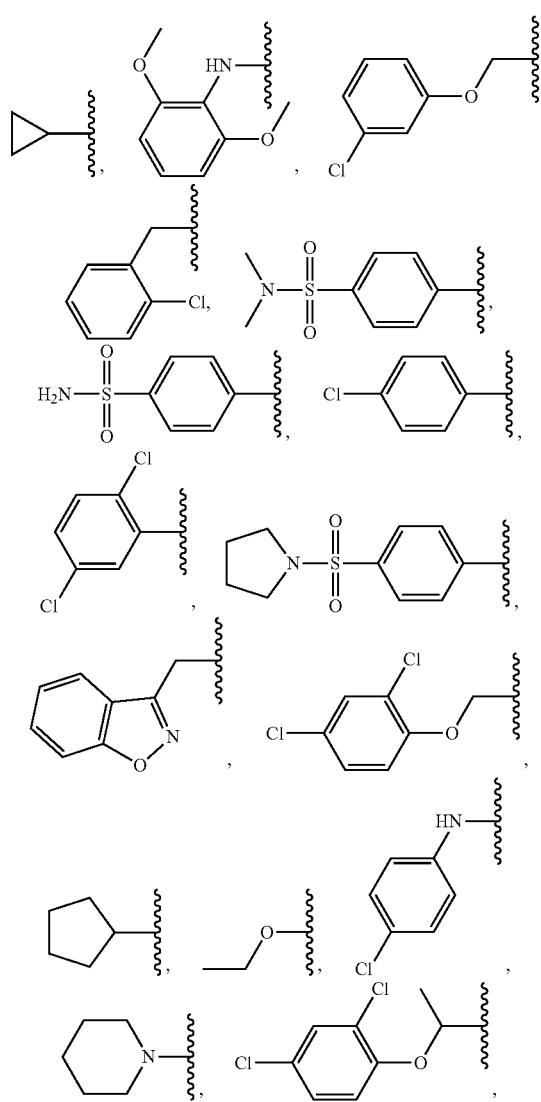

-continued

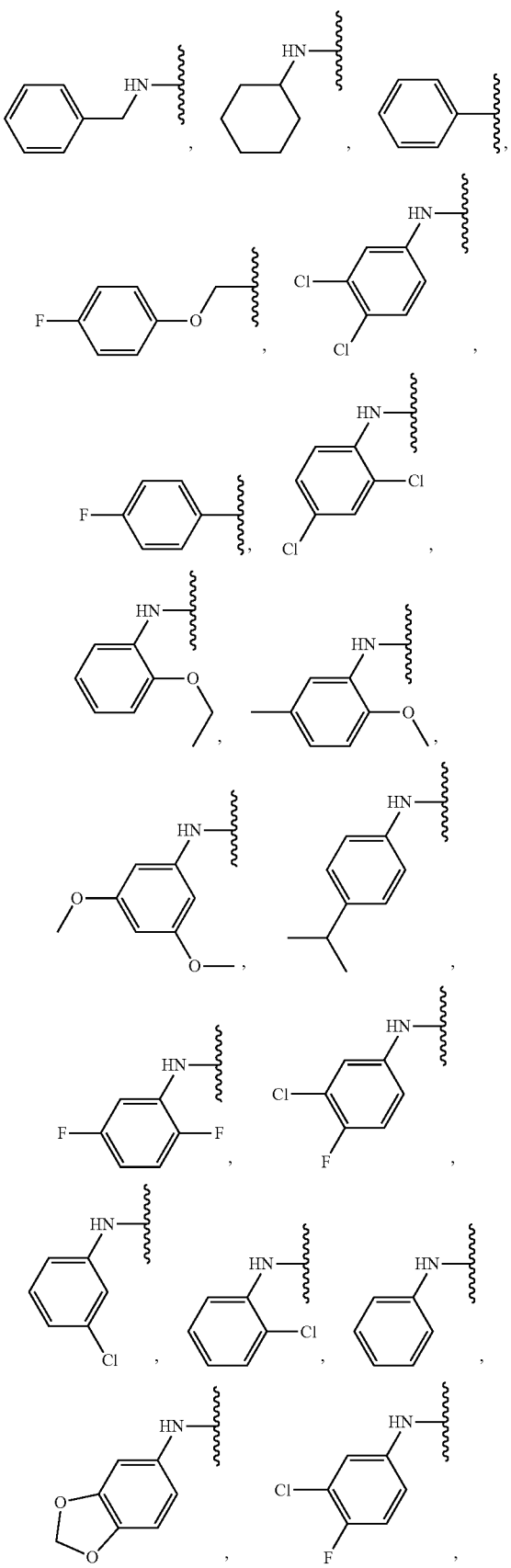

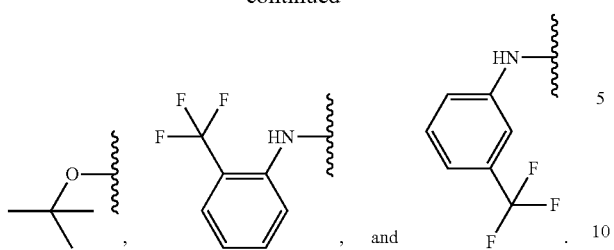

In an embodiment, the compound has the following structure:

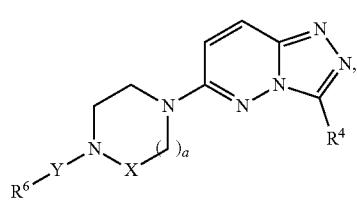
(III)

wherein Y is a bond, $S(O)_2$, or $CH_2$; $R^6$ is selected from the group consisting of substituted or unsubstituted $C_1$-$C_8$ alkyl group, including all integer numbers of carbons and ranges of numbers of carbons therebetween, substituted or unsubstituted cycloalkyl group, substituted or unsubstituted benzyl group, substituted or unsubstituted phenyl group, and substituted or unsubstituted heteroaryl group; X is $CH_2$ or C=O; and a is 1 or 2.

In an embodiment, the compound has the following structure:

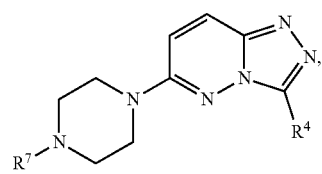
(IV)

where $R^7$ is a substituted or unsubstituted $C_1$-$C_8$ alkyl group.

In an embodiment, the compound has the following structure:

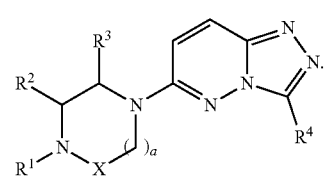
(V)

In an embodiment, the compound has the following structure:

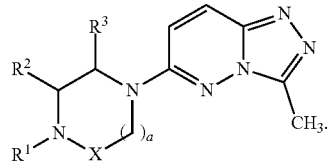
(VI)

In an embodiment, the compound has the following structure:

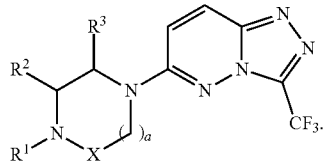
(VII)

In an embodiment, the compound has the following structure:

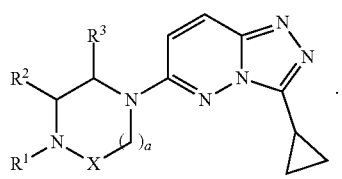
(VIII)

In an embodiment, the compound has the following structure:

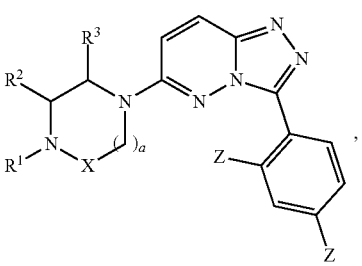
(IX)

where Z is independently selected from the group consisting of hydrogen and fluorine atom.

The compounds referred to in this disclosure as MMV665917, MMV675977, and MMV672987 have the following structures:

MMV665917
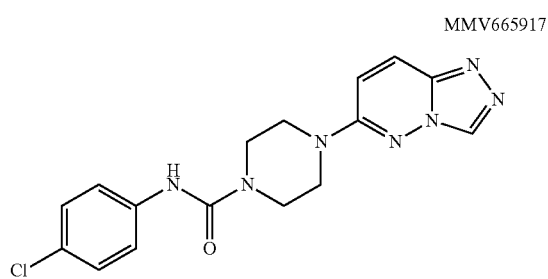
MMV675977
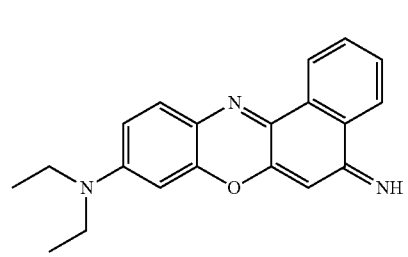
MMV672987
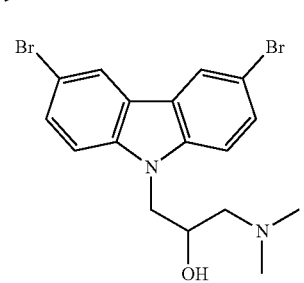
In an embodiment, the disclosure provides a method for treating an individual diagnosed with or suspected of having a *cryptosporidium* infection comprising administering to the individual a therapeutically effective amount of one or more of the following compounds:
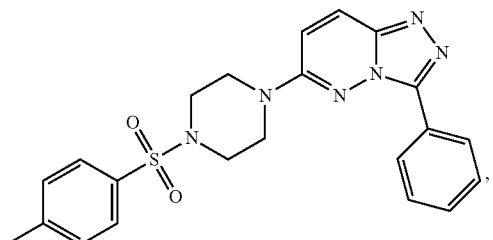
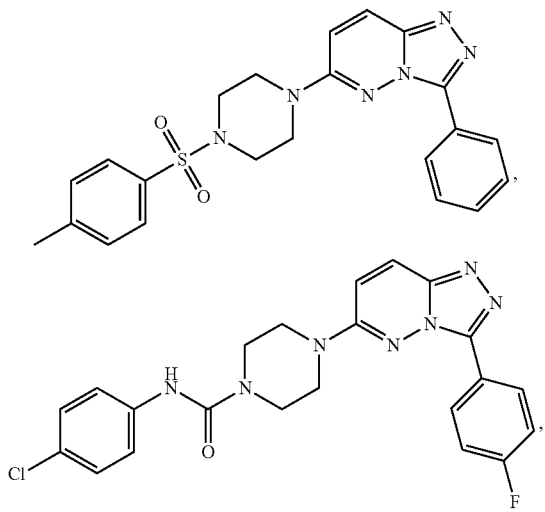
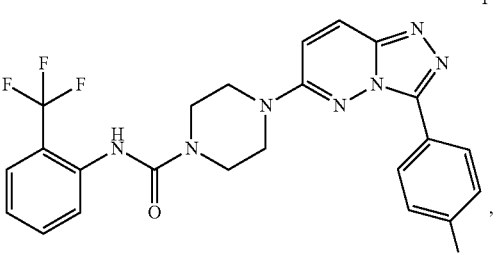
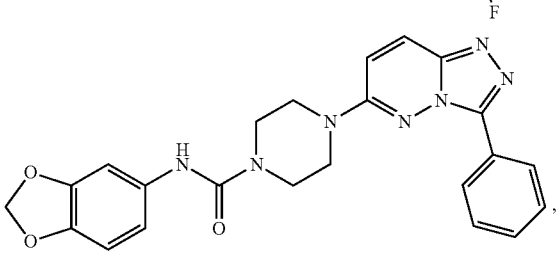
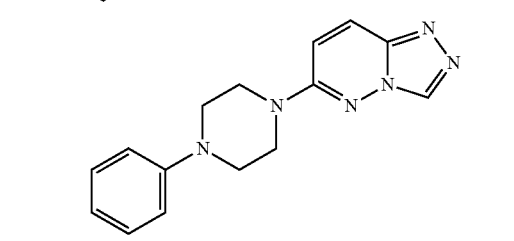
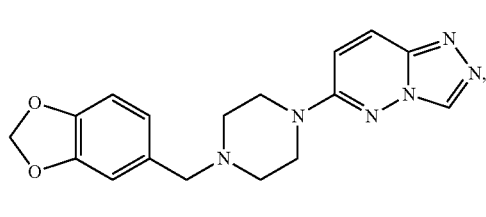
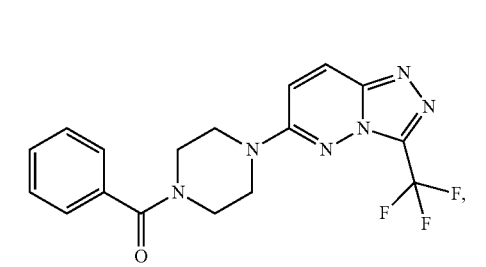

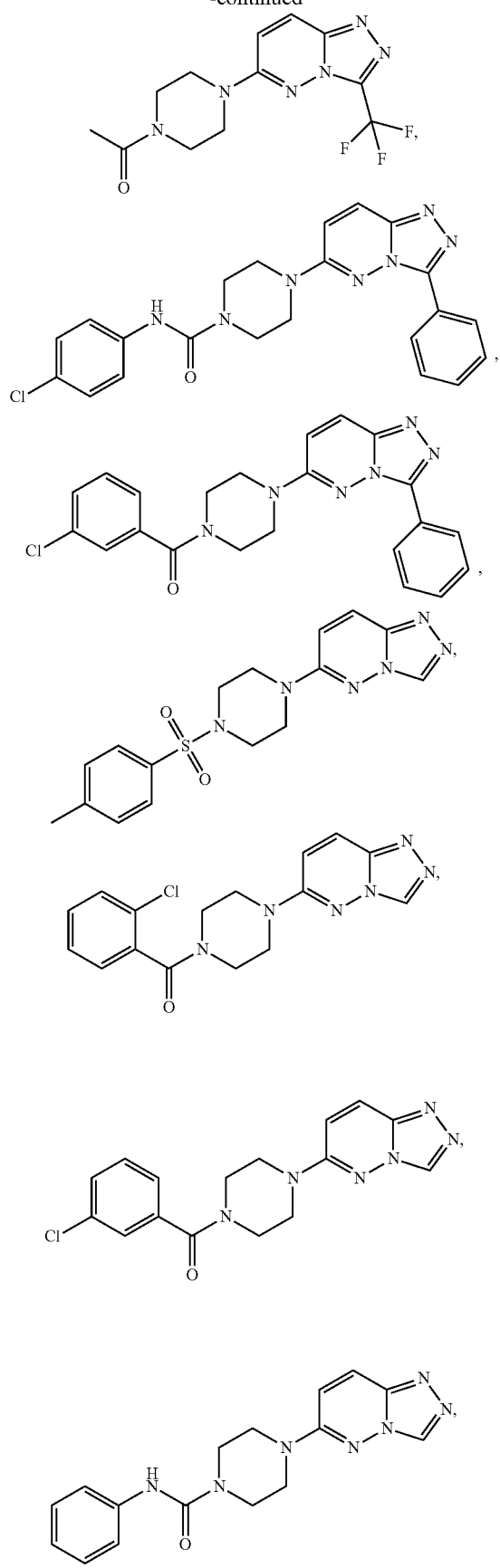
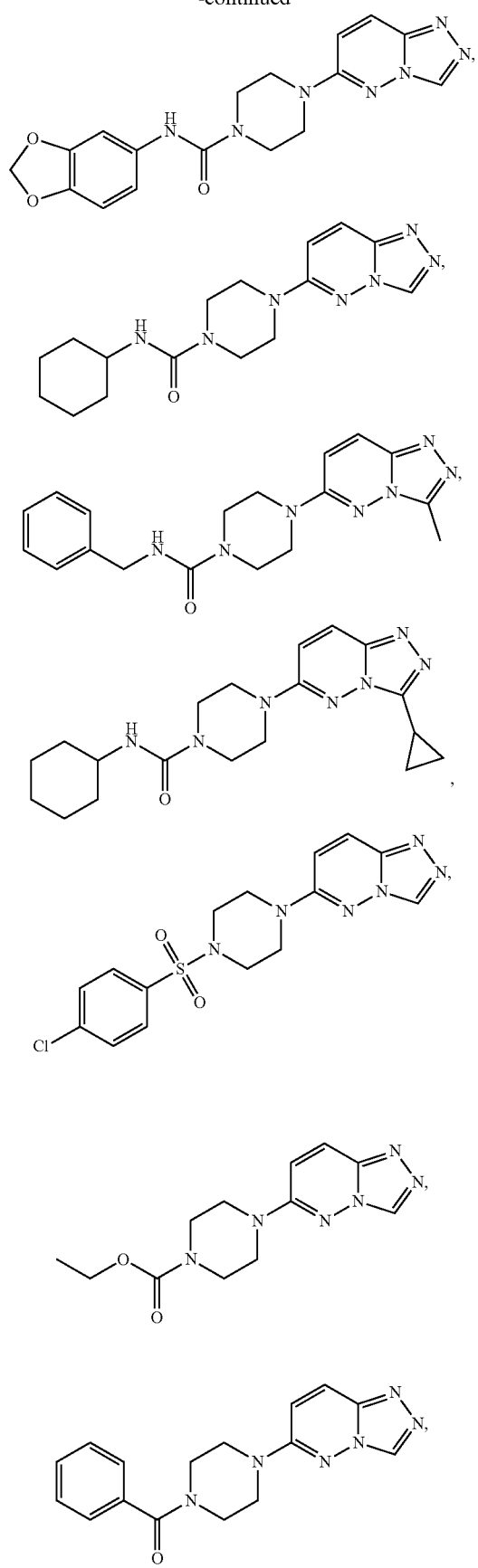

15
-continued
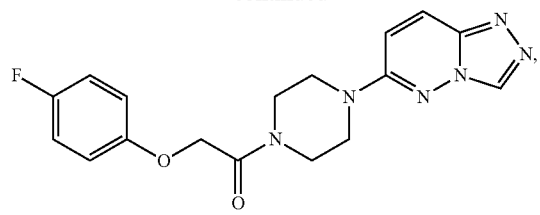
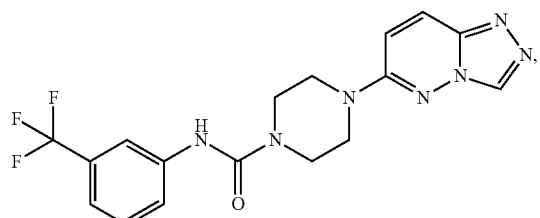
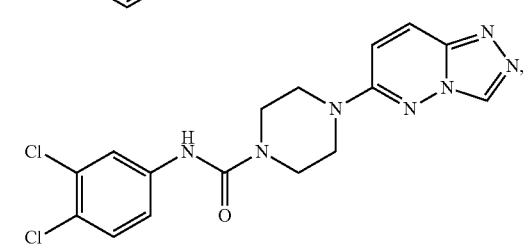
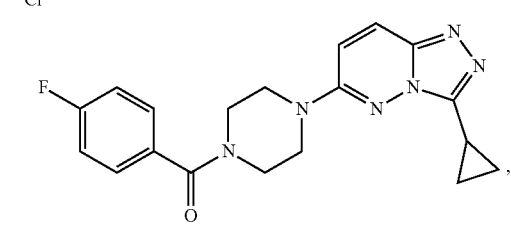
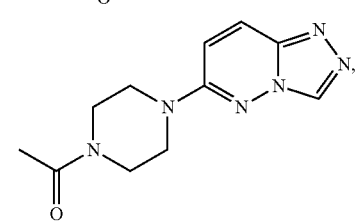
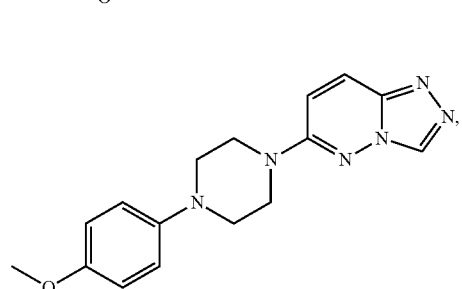
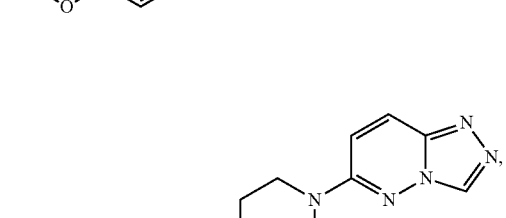
16
-continued
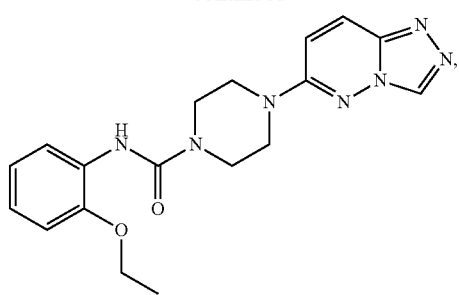
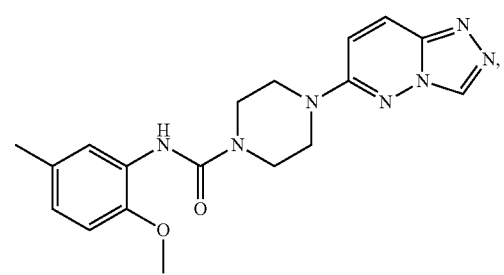
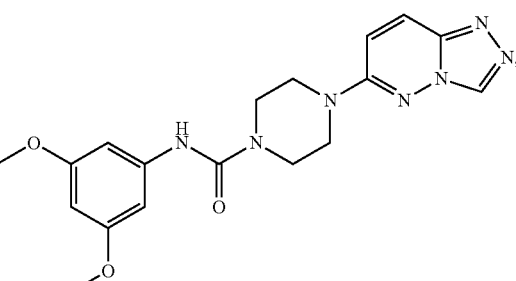
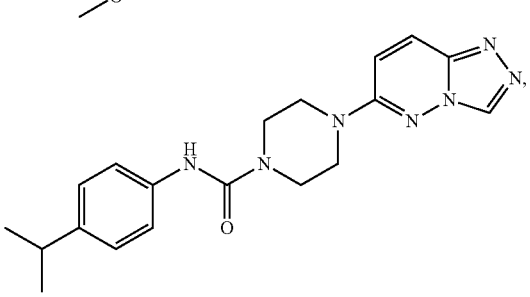
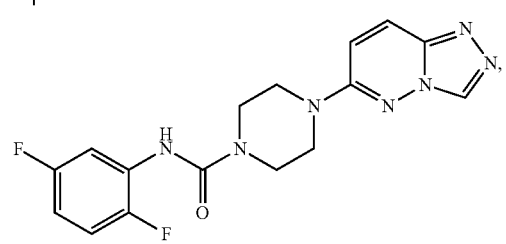
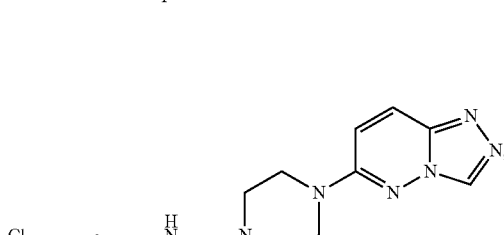

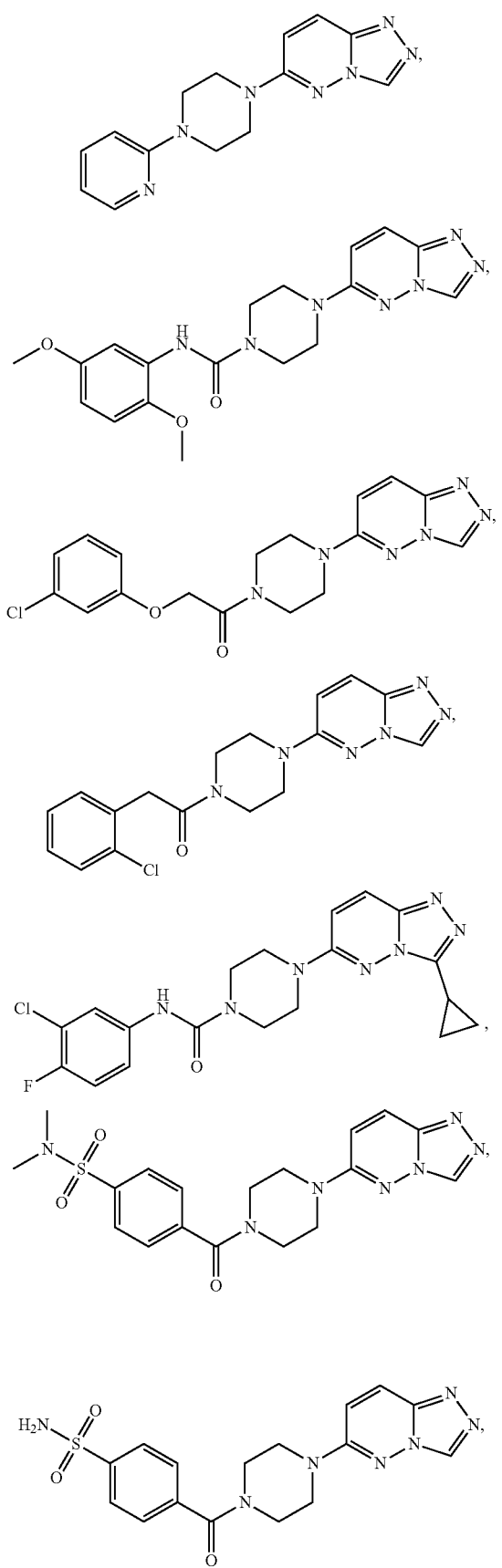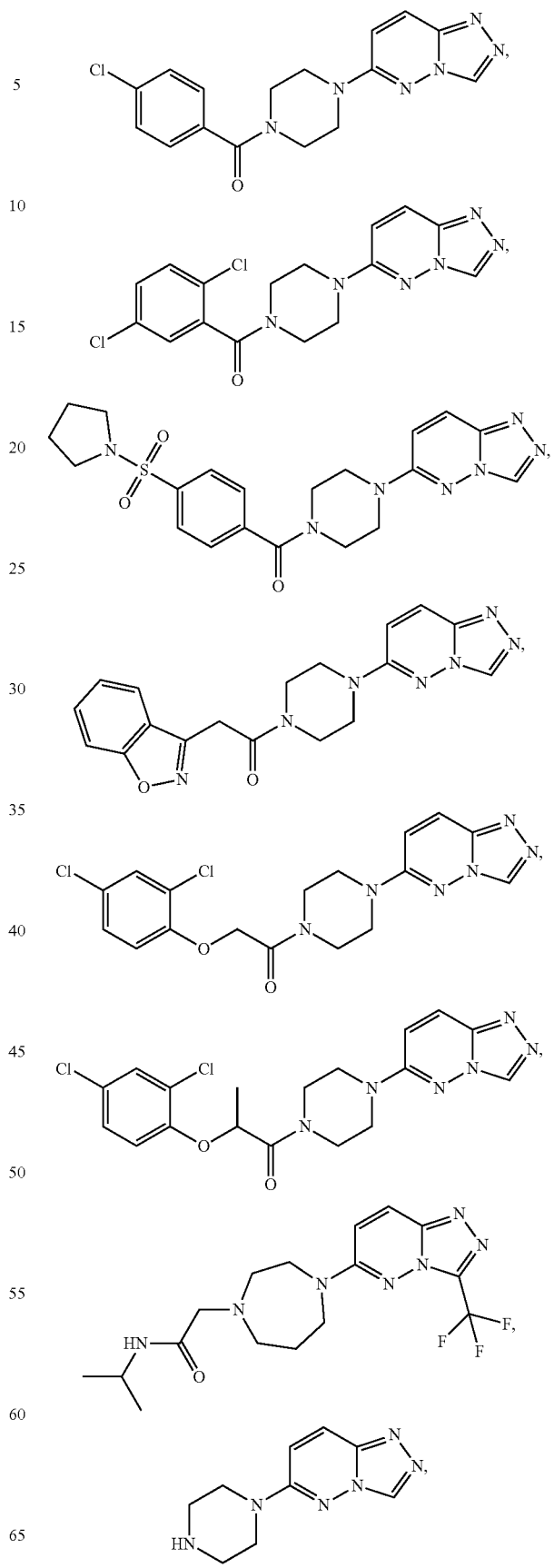

-continued
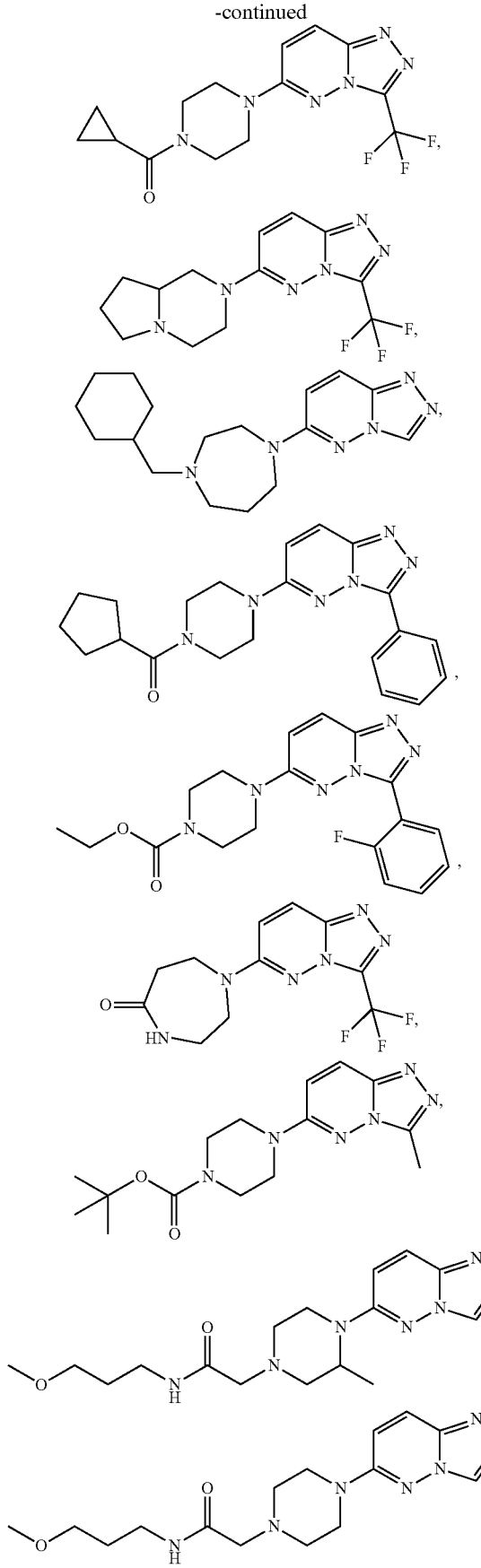
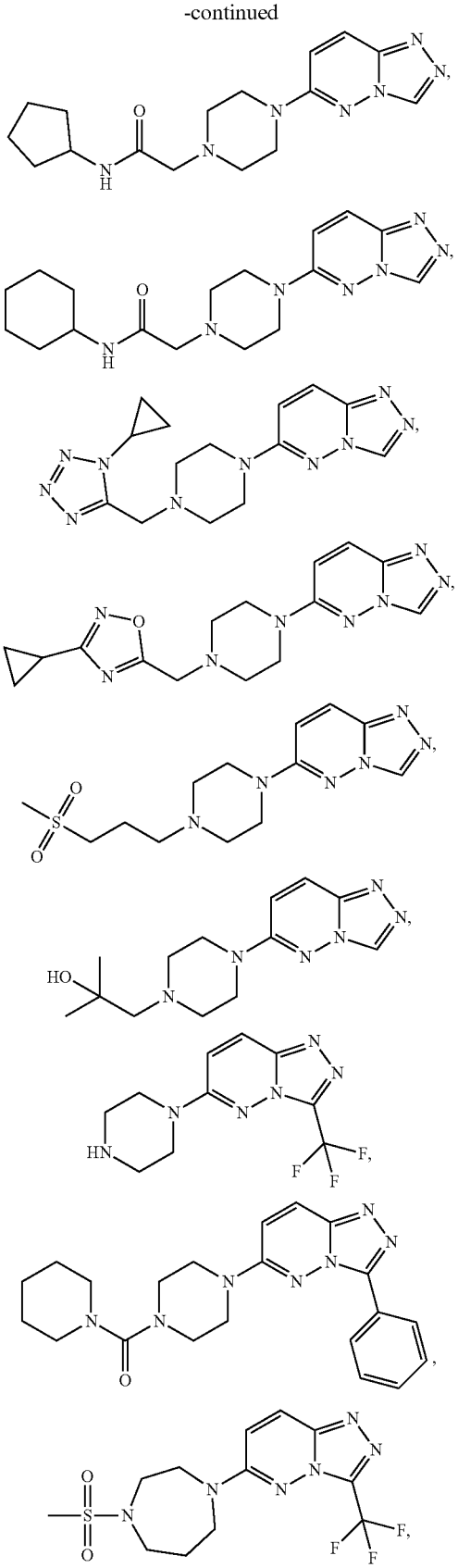

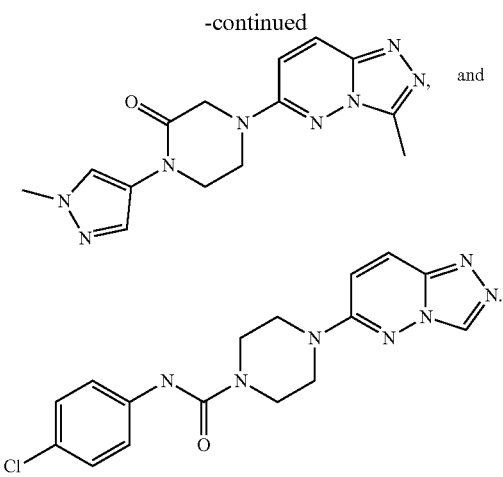

The compounds exhibit wide variability in pharmacokinetic and physicochemical properties while still retaining desirable biological activity as described herein (see, for example, FIG. 4). For example solubility, e.g., log P, is variable while still retaining desirable biological activity as described herein.

The compounds may be used to treat a *cryptosporidium* infection caused by any species of *Cryptosporidium*. Examples of *Cryptosporidium* species include, *Cryptosporidium parvum* or *Cryptosporidium hominis*.

The individual to be treated by the method of the disclosure may be human or non-human. Non-human animals include ungulates such as bovines.

In an aspect the present disclosure provides a composition for administration to an individual. For example a composition comprises a pH sensitive polymer.

In an embodiment the composition comprises a compound of the present disclosure encapsulated in a pH sensitive polymer suitable for release of a compound of the disclosure in the small intestines, distal small intestine, or colon.

In an embodiment, the pH sensitive polymer suitable for such a release can be a synthetic anionic polymer based on a monomer such as acrylic acid, methacrylic acid, propionic acid, 2-acrylmido-2-methylpropylsulfonic acid, 2-methacryloxyethylsulfonic acid, 3-methacryloxy-2-hydroxypropylsulfonic acid, ethylenesulfonic acid, styrenesulfonic acid, sulfoxyethyl methacrylate, or a combination thereof. In another embodiment, the anionic polymer can be a natural anionic polymer such as hyaluronic acid, alginic acid, carboxymethyl cellulose, carboxymethyl dextran, poly(aspartic acid), or heparin. Several commercial pH sensitive polymers are available. For example, Eudragit L, Eudragit S from Röhm Pharma GmBH (based on methacrylic acid and methyl methacrylate) or CMEC from Freund Sangyo Co., Ltd; CAP from Wako Pure Chemicals Ltd.; or HP-50 and ASM from Shin-Etsu Chemical Co., Ltd. (derived from cellulose) can be used.

Without intending to be bound by any particular theory it is considered that compounds with adequate solubility to access the parasites within intestinal epithelial cells are desired. In an embodiment, the compounds are largely retained at the site of infection within the gut. Consistent with the ability of achieving this goal, the SAR studies conducted demonstrate that formulations of each of these chemical scaffolds with widely divergent solubility (and, therefore, systemic absorption) have retained potency against *Cryptosporidium* within intestinal epithelial cells. In essence, compounds for treatment of cryptosporidiosis should break several of Lipinski's rules for selection of drug leads. Thus, formulations of each scaffold that are optimized for treatment of cryptosporidiosis will be distinct from formulations appropriate for treatment of a systemic infection such as malaria. Drug exposure (both the ability to penetrate the cell and parasitophorous vacuole, and retention at the site of infection rather than oral absorption) will be equivalent. In an embodiment, the compounds are not released systemically but are rather retained in the gastrointestinal tract. In an embodiment, the compounds of the method are taken up by the cells of the lumen of the gastrointestinal tract. In another embodiment, systemic exposure may be necessary in certain cases. For example, in severely immunocompromised people such as those with AIDS, infection can involve the biliary tree and, rarely, even the lungs. In these circumstances, a drug or formulation that favors systemic absorption, and/or enterohepatic recirculation may be desirable.

In an embodiment, a formulation comprising a compound of the disclosure is formulated in a manner such that an extended release in the small intestines, distal small intestine, or colon is achieved. For example, pH sensitive polymers can be used as described herein.

In an aspect, the present disclosure provides a composition comprising at least one compound of the disclosure. Compositions comprising at least one compound of the disclosure include, for example, pharmaceutical preparations.

The present disclosure includes all possible stereoisomers and geometric isomers of a compound of the present disclosure. The present disclosure includes both racemic compounds and optically active isomers. When a compound of the present disclosure is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of a compound of the present disclosure are possible, the present disclosure is intended to include all tautomeric forms of the compounds.

Prodrugs of a compound of the present disclosure also can be used as the compound in a method of the present disclosure. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)).

Compounds of the present disclosure can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the disclosure can exist as salts. Pharmaceutically acceptable salts of the compounds of the disclosure generally are preferred in the methods of the disclosure. As used herein, the term "pharmaceutically acceptable salts"

refers to salts or zwitterionic forms of a compound of the present disclosure. Salts of compounds having the structure (I) to (XII) can be prepared during the final isolation and purification of the compounds or separately by reacting the compound with an acid having a suitable cation. The pharmaceutically acceptable salts of a compound of the present disclosure are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include a compound of the present disclosure as well as pharmaceutically acceptable salts, hydrates, or prodrugs thereof.

Compositions comprising a compound of the disclosure and a pharmaceutical agent can be prepared at a patient's bedside, or by a pharmaceutical manufacture. In the latter case, the compositions can be provided in any suitable container, such as a sealed sterile vial or ampoule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described herein can include one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The dose of the composition comprising a compound of the disclosure and a pharmaceutical agent generally depends upon the needs of the individual to whom the composition of the disclosure is to be administered. These factors include, for example, the weight, age, sex, medical history, and nature and stage of the disease for which a therapeutic or prophylactic effect is desired. The compositions can be used in conjunction with any other conventional treatment modality designed to improve the disorder for which a desired therapeutic or prophylactic effect is intended, non-limiting examples of which include surgical interventions and radiation therapies. The compositions can be administered once, or over a series of administrations at various intervals determined using ordinary skill in the art, and given the benefit of the present disclosure.

Compositions of the disclosure can comprise more than one pharmaceutical agent. For example, a first composition comprising a compound of the disclosure and a first pharmaceutical agent can be separately prepared from a composition which comprises the same compound of the disclosure and a second pharmaceutical agent, and such preparations can be mixed to provide a two-pronged (or more) approach to achieving the desired prophylaxis or therapy in an individual. Further, compositions of the disclosure can be prepared using mixed preparations of any of the compounds disclosed herein.

It is envisioned, therefore, that a compound of the present disclosure is useful in the treatment of a *cryptosporidium* infection. Thus, the present disclosure concerns the use of a compound of the present disclosure, or a pharmaceutically acceptable salt thereof, or a pharmaceutical composition containing either a compound of the present disclosure, or a pharmaceutically acceptable salt thereof, for the manufacture of a medicament for the treatment of such conditions and diseases.

*Cryptosporidium* infection is defined as detection of *Cryptosporidium* in the feces, by any standard means such as microscopic parasite exam, antigen detection, and polymerase chain reaction. In some instances, such individuals may be suffering from diarrhea, but may be asymptomatic where there are indications to treat for prevention of long-term sequelae (such as malnutrition and growth stunting) and for prevention of spreading infection to others. In areas where *Cryptosporidium* infection are highly endemic, treatment for cryptosporidiosis may be provided (alone or in combination with treatment for other enteric infections) for suspected infection without microbiologic confirmation.

The compounds of the present disclosure can be therapeutically administered as the neat chemical, but it is preferred to administer a compound of the present disclosure as a pharmaceutical composition or formulation. Thus, the present disclosure provides a pharmaceutical composition comprising a compound of the present disclosure together with a pharmaceutically acceptable diluent or carrier therefor. Also provided is a process of preparing a pharmaceutical composition comprising admixing a compound of the present disclosure with a pharmaceutically acceptable diluent or carrier therefor.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In one embodiment, the pharmaceutically-acceptable formulation is such that it provides sustained delivery of a compound of the present disclosure to an individual for at least 12 hours, 24 hours, 36 hours, 48 hours, one week, two weeks, three weeks, or four weeks after the pharmaceutically-acceptable formulation is administered to the individual.

In certain embodiments, these pharmaceutical compositions are suitable for oral administration to an individual. In other embodiments, as described in detail below, the pharmaceutical compositions of the present disclosure may be specially formulated for administration in solid or liquid form, including those adapted for the following: oral administration, for example, drenches (aqueous or non-aqueous solutions or suspensions), tablets, boluses, powders, granules, and pastes.

The compositions may conveniently be presented in unit dosage form and may be prepared by any methods well known in the art of pharmacy. The amount of active ingredient which can be combined with a carrier material to produce a single dosage form will vary depending upon the individual being treated, the particular mode of administration. The amount of active ingredient which can be combined with a carrier material to produce a single dosage form will generally be that amount of a compound of the present disclosure which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Compositions of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of a compound of the present disclosure include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to a compound of the disclosure, the composition may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

When a compound of the present disclosure are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

In certain embodiments, the methods of the disclosure include administering to an individual a therapeutically effective amount of a compound of the present disclosure in combination with another pharmaceutically active ingredient. Pharmaceutically active ingredients that may be used can be found in Harrison's Principles of Internal Medicine, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. A compound of the present disclosure and the pharmaceutically active ingredient may be administered to the individual in the same pharmaceutical composition or in different pharmaceutical compositions (at the same time or at different times).

Methods delineated herein include those wherein the individual is identified as in need of a particular stated treatment. Identifying an individual in need of such treatment can be in the judgment of an individual or a health care professional and can be subjective (e.g. opinion) or objective (e.g. measurable by a test or diagnostic method). In other methods, the individual is prescreened or identified as in need of such treatment by assessment for a relevant marker or indicator of suitability for such treatment.

The compounds and compositions disclosed in the present disclosure can also be used for prophylaxis in an individual who is at risk of being exposed to *cryptosporidium*. A prophylactic use may be useful, for example, in an individual who is about to undertake a journey to a region where an outbreak of *cryptosporidium* has been reported or is known to occur. For the prophylactic use, one or more doses of a composition comprising the compounds of the present disclosure may be administered. Dosing for prophylactic treatment may vary compared to dosing of known *cryptosporidium* infections. In one embodiment treatment may be given 1-3 times a day for 1 to 10 days or longer. In one embodiment, treatment is given for up to three times (such as 1 to 3 times) daily for up to 10 days (such as 1-10 days) in immunocompetent hosts. For immmuosuppressed hosts such as those with AIDS, long-term suppressive treatment may be warranted.

The identification of those patients who are in need of prophylactic treatment for a *Cryptosporidium* infection can readily identify such candidate patients, by the use of, for example, clinical tests, physical examination and medical/family history. The individual may have a *Cryptosporidium* infection, may be at risk of developing a *Cryptosporidium* infection, or may need prophylactic treatment prior to anticipated or unanticipated exposure to a condition(s) capable of increasing susceptibility to a *Cryptosporidium* infection. In an embodiment, those in need of prophylactic treatment for a *Cryptosporidium* infection can take a therapeutically effective amount of a compound of the present disclosure from 1 to 30 days prior to an anticipated or unanticipated exposure to a condition(s) capable of increasing susceptibility to a *Cryptosporidium* infection. In another embodiment, those in need of prophylactic treatment for a *Cryptosporidium* infection can take a therapeutically effective amount of a compound of the present disclosure from 1 to 24 hours prior to an anticipated or unanticipated exposure to a condition(s) capable of increasing susceptibility to a *Cryptosporidium* infection. In an embodiment, an individual can take a therapeutically effective amount of a compound of the present disclosure shortly after exposure to *Cryptosporidium* infection.

In another aspect, the disclosure provides a packaged composition including a therapeutically effective amount of a compound of the present disclosure and a pharmaceutically acceptable carrier or diluent. The composition may be formulated for treating an individual suffering from or susceptible to a *Cryptosporidium* infection, and packaged with instructions to treat an individual suffering from or susceptible to a *Cryptosporidium* infection.

In one aspect, the disclosure provides a kit for treating a *Cryptosporidium* infection in an individual is provided and includes a compound of the present disclosure, pharmaceutically acceptable esters, salts, and prodrugs thereof, and instructions for use. In certain embodiments, the disclosure provides: a kit for treating a *Cryptosporidium* infection, in an individual, the kit comprising a compound of the present disclosure. The kit may also include instructions for administration of the compound or composition. The instructions may include details on one or more of the following: dosage, frequency, number of administrations to be carried out (such as number of tablets to be consumed), whether the composition needs to be taken with food, water etc., storage of the composition, and the like.

For veterinary use, a compound of the present disclosure, or a pharmaceutically acceptable salt or prodrug, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, bovines or ungulates.

When administered in combination with other therapeutics, a present compound may be administered at relatively lower dosages. In addition, the use of targeting agents may allow the necessary dosage to be relatively low. Certain compounds may be administered at relatively high dosages due to factors including, but not limited to, low toxicity and high clearance.

For human use, a compound of the present disclosure can be administered alone, but generally is administered in admixture with a pharmaceutical carrier selected with regard to the intended route of administration and standard pharmaceutical practice. Pharmaceutical compositions for use in accordance with the present disclosure can be formulated in a conventional manner using one or more physiologically acceptable carrier comprising excipients and auxiliaries that facilitate processing of a compound of the present disclosure into pharmaceutical preparations.

In an aspect, a compound as described herein exhibits activity against *Cryptosporidium*. In certain embodiments, the *Cryptosporidium* infection is from the *Cryptosporidium parvum, Cryptosporidium hominis, Cryptosporidium andersoni*, or a combination thereof. In various embodiments, the compounds of the disclosure are those which display in vitro $IC_{50}$ values upwards of 4.54 µM against *Cryptosporidium parvum*.

As appreciated by persons skilled in the art, additional active or ancillary agents can be used in the methods described herein. Reference herein to treatment also extends to prophylaxis, as well as to treatment of established diseases or symptoms.

The present disclosure can be applied to cell populations ex vivo. For example, the present compounds can be used ex vivo to determine the optimal schedule and/or dosing of administration of the present compound for a given indication, cell type, patient, and other parameter. Information gleaned from such use can be used for experimental purposes or in the clinic to set protocol for in vivo treatment. Other ex vivo uses for which the disclosure is suited are apparent to those skilled in the art.

The steps of the method described in the various embodiments and examples disclosed herein are sufficient to treat an individual diagnosed with or suspected of having a *cryptosporidium* infection or a method for prophylaxis in an individual diagnosed with or suspected of having a *cryptosporidium* infection. Thus, in an embodiment, the method consists essentially of a combination of the steps of the method disclosed herein. In another embodiment, the method consists of such steps.

In the following Statements, various examples of the methods, compositions, and kits of the present disclosure are described:

1. In an example, a method for treating an individual diagnosed with or suspected of having a *cryptosporidium* infection or prophylaxis in an individual who is at risk of having a *cryptosporidium* infection comprises administering (e.g., by any method disclosed herein) to the individual (e.g., an individual disclosed herein) a compound or a composition comprising a therapeutically effective or a prophylactically effective amount of the compound having the following structure:

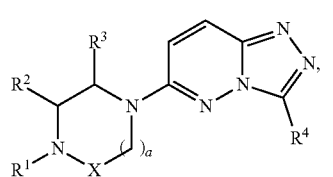
(I)

where $R^1$ is selected from the group consisting of hydrogen atom, $C_1$-$C_8$ alkyl group, sulfonyl group having the structure: —S(O)$_2$R, and carbonyl containing group having the structure: —C(O)R, —C(O)$_2$R, or —C(O)N(R)$_2$, where R is independently at each occurrence selected from the group consisting of hydrogen atom, $C_1$-$C_9$ alkyl group, heteroaryl group, alkoxy group, amino group, phenyl group, benzyl group, heteroaryl group, and —CH$_2$-heteroaryl group comprising 1 to 4 O and/or N atoms;

$R^2$ is a hydrogen atom, or it may also combine with $R^1$ to form

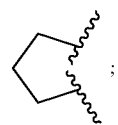

$R^3$ is a hydrogen atom or a $C_1$-$C_9$ alkyl group; $R^4$ is selected from the group consisting of hydrogen atom, $C_1$-$C_9$ alkyl group, $C_3$-$C_6$ cycloalkyl group, haloalkyl group, and phenyl derivative having the structure:

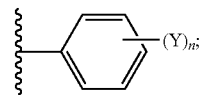

where Y is independently selected from the group consisting of F, Cl, Br, and I, and n can be 0, 1, 2, 3, 4, or 5; X is —CH$_2$ or C=O; and a is 1 or 2.

2. In another example, a method is the method of Statement 1 in which the compound has the following structure:

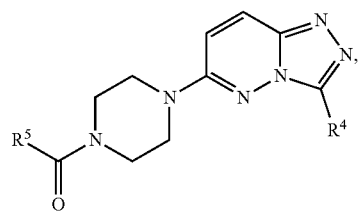
(II)

where $R^5$ is selected from the group consisting of alkyl group, $C_3$ to $C_6$ cycloalkyl group, benzyl group, amino group, phenyl group, alkoxy group, alkylheterocyclic group, phenoxy group, and aniline group.

3. In another example, a method is the method of Statement 2 in which $R^5$ is selected from the group consisting of the $R^5$ groups disclosed herein.

4. In another example, a method is the method of Statement 1 in which the compound has the following structure:

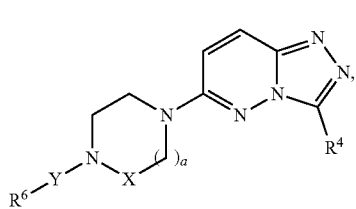
(III)

where Y is a bond, —S(O)$_2$, or —CH$_2$; $R^6$ is selected from the group consisting of $C_1$-$C_8$ alkyl group, cycloalkyl group, benzyl group, phenyl group, and heteroaryl group; X is —CH$_2$ or C=O; and a is 1 or 2.

5. In another example, a method is the method of Statement 1 in which the compound has the following structure: where R$^7$ is a C$_1$-C$_8$ alkyl group.

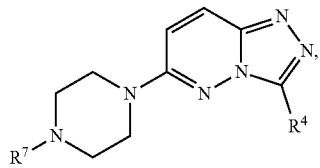
(IV)

6. In another example, a method is the method of Statement 1 in which the compound has the following structure:

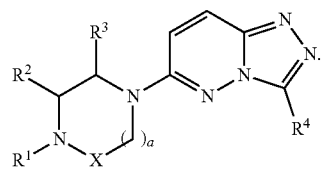
(V)

7. In another example, a method is the method of Statement 1 in which the compound has the following structure:

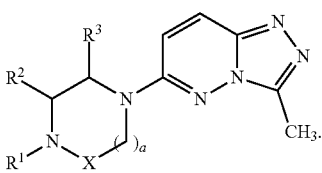
(VI)

8. In another example, a method is the method of Statement 1 in which the compound has the following structure:

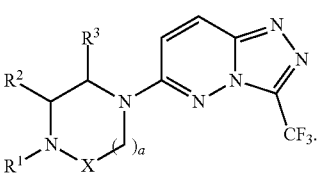
(VII)

9. In another example, a method is the method of Statement 1 in which the compound has the following structure:

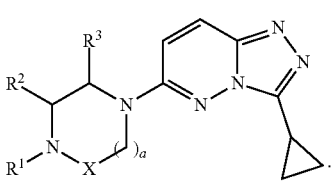
(VIII)

10. In another example, a method is the method of Statement 1 in which the compound has the following structure:

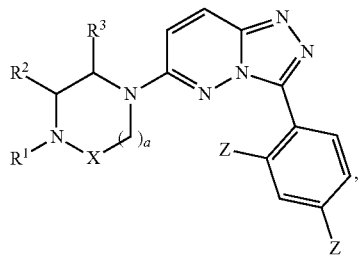
(IX)

wherein Z is independently selected from the group consisting of hydrogen and fluorine atom.

11. In another example, a method is the method of Statement 1 in which the compound is selected from a compound disclosed herein and combinations thereof.

12. In another example, a method is the method of any one of the preceding Statements in which the *cryptosporidium* infection is caused by *Cryptosporidium parvum*, *Cryptosporidium hominis*, or *Cryptosporidium andersoni*.

13. In another example, a method is the method of any one of the preceding Statements in which the individual is human or non-human animal (e.g., bovine, or ungulate).

14. In an example, a composition for oral administration comprises a compound disclosed herein (e.g., a compound of any one of the preceding Statements) encapsulated in a pH sensitive polymer suitable for release of the compound in the small intestines, distal small intestine, or colon.

15. In an example, a kit comprises a compound or a composition disclosed herein (e.g., a compound or composition of any one of the preceding Statements) and instructions on administration details to an individual who has been diagnosed with or who is at risk of getting *cryptosporidium* infection wherein said details comprise one or more of the following: dosage, frequency, and length of time for administration of the composition.

The following examples are presented to illustrate the present disclosure. They are not intended to be limiting in any manner.

Example 1

In this example, a cell-based screening assay was utilized to identify novel *Cryptosporidium parvum* growth inhibitors, and an immunocompromised mouse model for in vivo validation of identified drug screening hits was identified.

Materials and Methods: Cell culture and *Cryptosporidium* infections: The high throughput screen for *C. parvum* growth inhibitors was carried out using human ileocecal adenocarcinoma (HCT-8) cells (ATCC) maintained in RPMI 1640 medium with HEPES, sodium pyruvate (1 mM) and L-glutamate with 10% horse serum (ATCC) supplemented with 120 U/mL penicillin and 120 µg/mL streptomycin. HCT-8 cells were grown to confluence in 384-well, tissue culture-treated, black-walled, clear-bottom microwell plates (BD Falcon). Cells were then inoculated with 5.5×10$^3$/well *C. parvum* (Bunchgrass Farms, Deary, Id.) oocysts, which had been primed for excystation with 10 mM HCl and 2 mM sodium taurocholate and then resuspended in inoculation medium (as described above without horse serum). Infected cells were incubated for three hours at 37° C. at which point an equal volume of growth medium (with experimental compounds added in the case of confirmatory assays or without in the case of the HTS; see below) with 20% horse serum was added, and cells were incubated for an additional 48 hours (except for minimum effective exposure experiments, which were incubated for 72 hours).

Experimental Compounds:

The MMV Open Access Malaria Box was diluted to a final concentration of 1.67 mM and arrayed into the center 308 wells of V-bottom polypropylene 384-well source plates (Whatman) and stored at −80° C. until use. Source plates were warmed to 37° C. and briefly centrifuged prior to use. A 384 solid pin Multi-Blot replicator tool (V&P scientific) was used to transfer approximately 70 nL of compound to the assay plate for a final concentration of approximately 2.3 µM. Controls on each plate included wells containing DMSO only (vehicle) and nitazoxanide at a stock concentration that resulted in a final concentration approximately equal to the 90% inhibitory concentration ($IC_{90}$=6.6 µM).

Hit Definition:

A screening hit was defined as any compound that inhibited the average C. parvum parasite count from duplicate screening plates by greater than 65%, a cutoff that corresponded to reduction by greater than 2 standard deviations from the mean reduction in parasite counts from the compound library as a whole.

In Vitro Dose Response Assays:

Compounds that met the hit definition above were purchased from commercial sources and used for secondary in vitro and in vivo studies. Purchased compounds were used to generate in vitro dose-response curves using varied concentrations for each compound.

Immunofluorescence Assay for C. parvum Detection:

Infected monolayers were washed three times with PBS containing 111 mM D-galactose using an EL406 automated plate washer (Biotek), fixed with 4% paraformaldehyde, permeabilized with 0.25% Triton X-100 in PBS, and then blocked with 4% bovine serum albumin (BSA). Vegetative forms of C. parvum were detected by the addition of biotinylated Vicia villosa lectin (VVL; Vector Laboratories) and streptavidin-conjugated Alexa Fluor 568 (Invitrogen) diluted in PBS with 1% BSA and 0.1% Tween 20. Nuclei were counterstained with 0.29 mM Hoechst 33258 (Anaspec), and washed five times with PBS containing 0.1% Tween 20. Plates were then imaged with a Nikon Eclipse Ti2000 epifluorescent microscope with motorized stage and Exi blue fluorescent microscopy camera (QImaging). NIS-Elements Advanced Research software (Nikon USA) was used to automate acquisition of a three-by-three 20× field image from the center of each of the middle 308 wells of the assay plate (corresponding to approximately 13% of the total surface area of the well). Images were exported into ImageJ, which was used to execute the batch process function to execute previously validated macros to enumerate nuclei and parasites.

Data Handling and Analysis:

ImageJ outputs were imported into Microsoft Excel for data organization and analysis. Percent inhibition was calculated (equation 1) for each well in order to normalize the data and to facilitate the combination of data from individual biological replicates. Additional analysis and figure construction was conducted using GraphPad Prism6 v. 6.00 and Vortex $$\% \text{ inhibition} = \frac{\# \text{ parasites}_{DMSO\ treated\ wells} - \# \text{ parasites}_{experimental\ compound\ treated\ wells}}{\# parasites_{DMSO\ treated\ wells}} \quad (1)$$

Dose Response Curves.

Parasite counts were averaged for each infected well treated with a different concentration of experimental compound (n=11 wells) and 3 uninfected wells treated with the corresponding concentration of drug (to assess for non-specific background staining). The average value for all uninfected wells was subtracted from all parasite counts to adjust for background signal. Percent inhibition values were averaged for all of the wells in each treatment condition and the data from at least two biological replicates were combined to generate dose-response curves in GraphPad Prism. $IC_{50}$ values were calculated using the log[inhibitor] versus response—variable slope equation (equation 2) with the bottom and top constraints set equal to 0 and 100, respectively.

$$Y = \text{Bottom} + \frac{(\text{Top} - \text{Bottom})}{(1 + 10^{LogIC50 - X * Hill\ Slope})} \quad (2)$$

NOD SCID Gamma Immunocompromised Mouse Model of Cryptosporidiosis:

A NOD SCID gamma mouse model was used for in vivo testing of confirmed screening hits. NOD SCID gamma mice (Jackson Laboratories) develop Cryptosporidium parvum infection following oral gavage that is characterized by persistent infection of the small intestinal and cecal epithelium. The mice remain asymptomatic and gain weight normally. Infection is established by oral gavage of $1 \times 10^4$ C. parvum (Iowa strain) oocysts on day −6. Fecal parasite shedding is quantified by quantitative PCR of genomic DNA, using a standard curve generated by spiking oocysts into fecal samples from uninfected mice. Fecal oocyst shedding reliably becomes detectable at day 1 (1 week after infection). Experimental compounds are administered by oral gavage of 30 mg/kg in DMSO:1% HPMC (5:95) twice daily for 4 days. Parasite shedding is compared to that for infected mice treated with drug carrier alone (i.e. DMSO:1% HPMC (5:95)).

Results.

Structures and in vitro $EC_{50}$ values for inhibition of C. parvum development in HCT-8 cells for screening hits with confirmed activity can be seen in FIG. 1. $EC_{50}$ values of these hits ranged from 0.11 µM to 6.4 µM, with MMV665917 demonstrating in vitro potency.

Figure 2:
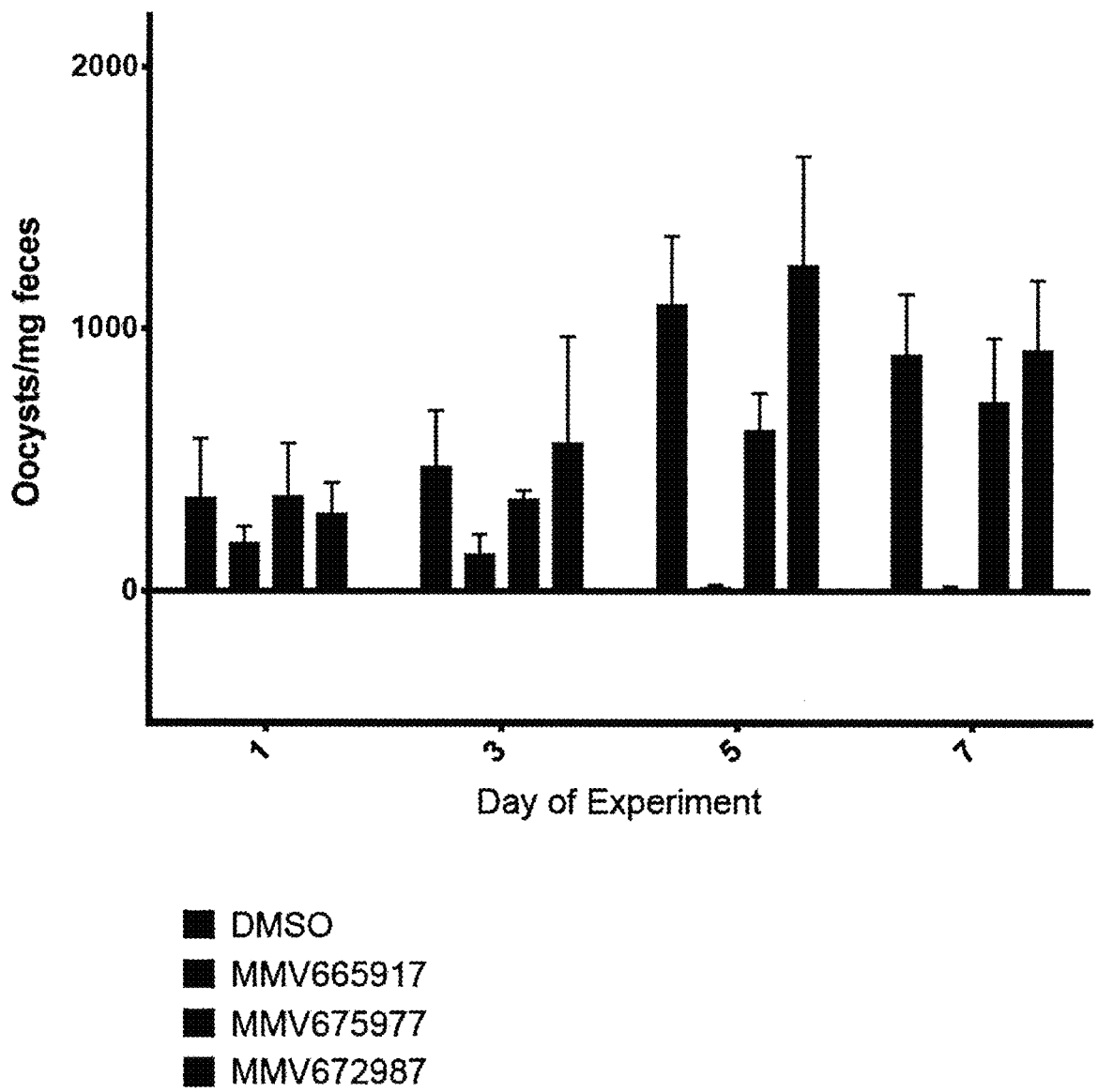
FIG. 2 shows the anti-parasitic effect of MMV665917 on *C. parvum* levels in mice over a 7 day period. Mice were infected with *C. parvum* one week prior to experiment and then administered doses (30 mg/kg) of either MMV665917, MMV675977, MMV672987 or DMSO twice daily by oral gavage on days 1-4. The number of oocysts/mg in collected feces were quantified by qPCR. For each set of data for a day, the bars from left to right are: DMSO, MMV665917, MMV675977, and MMV672987.

Results for treatment of C. parvum infected NOD SCID gamma mice with DMSO or selected MMV Malaria Box screening hits with confirmed in vitro activity given by oral gavage of 30 mg/kg twice daily on days 1-4 can be seen in FIG. 2. Cryptosporidium parvum infection was established on day −6. Parasite shedding is detectable in all animals on day 1. MMV665917 significantly reduced parasite shedding, which persisted for >3 days following cessation of treatment. Other compounds and DMSO had no effect. Data shown are the mean and SE for parasites detected/mg of feces (n=4 animals per treatment group).

Figure 5:
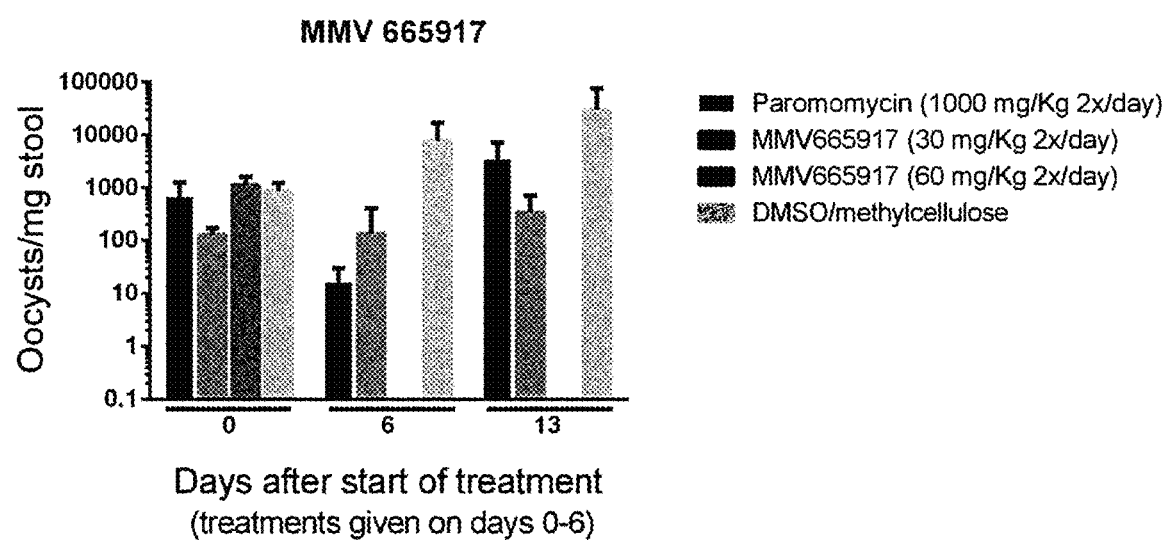
FIG. 5 shows data from a repeat of the experiment shown in FIG. 2, except that two different dosing regimens of MMV665917 were used. After infection with *C. parvum* one week prior to compound dosing, mice were treated by oral gavage with either MMV665917 at 30 mg/kg twice daily or 60 mg/kg twice daily for seven days. Mice treated with DMSO or Paromomycin 1000 mg/kg twice daily served as negative and positive controls. As before, mice treated with paromomycin relapsed quickly after treatment cessation. In this experiment, mice treated with 60 mg/kg twice daily MMV665917 were cured, but, in contrast to the experiment in FIG. 2, 30 mg/kg twice daily MMV665917 was not effective.
Figure 6:
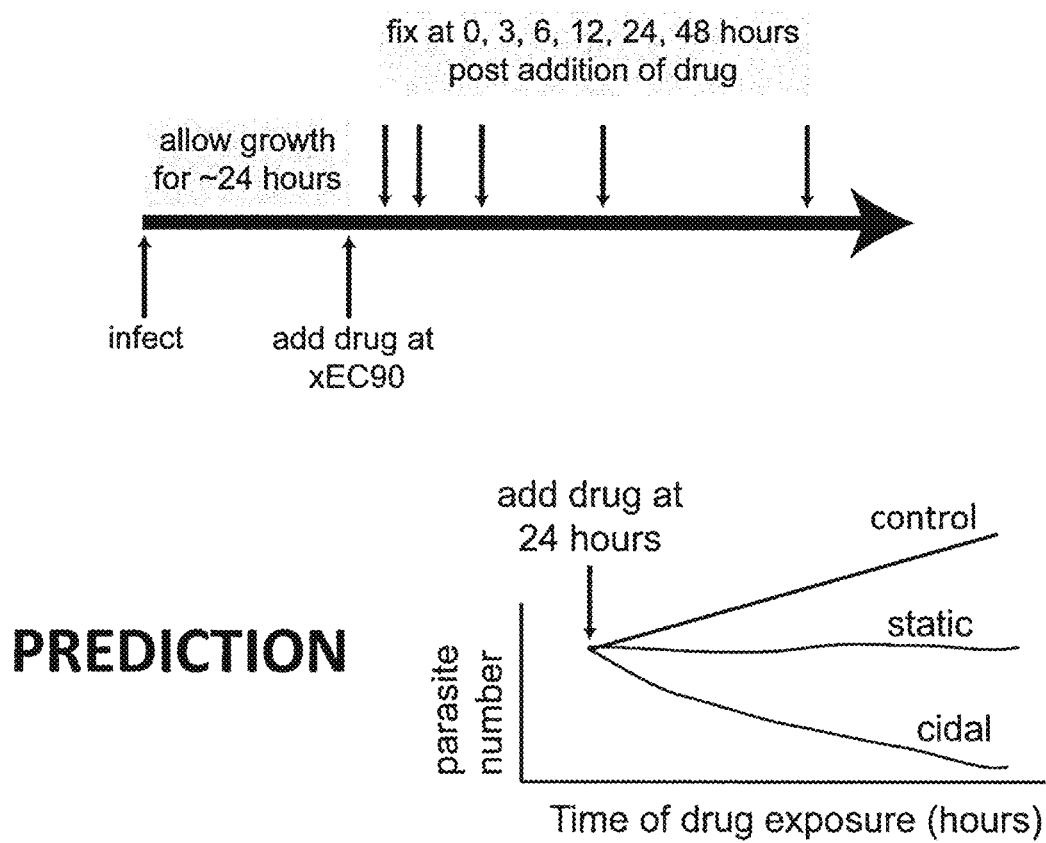
FIG. 6 shows a schematic for the experimental strategy to determine if MMV665917 is static or cidal for *C. parvum*, and the concentration of compound required to maximize the rate of parasite elimination. HCT-8 cell monolayers are infected and parasites are allowed to replicate for 24 hours before addition of experimental drug compounds. Parasite numbers are then measured at different time points following compound addition by epifluorescence microscopy, using the same method as used in FIG. 1. The cartoon shows the expected results for cidal or static compounds, with static compounds simply preventing further expansion of the parasite numbers after compound addition and cidal compounds expected to result in parasite elimination over time.
Figure 7:
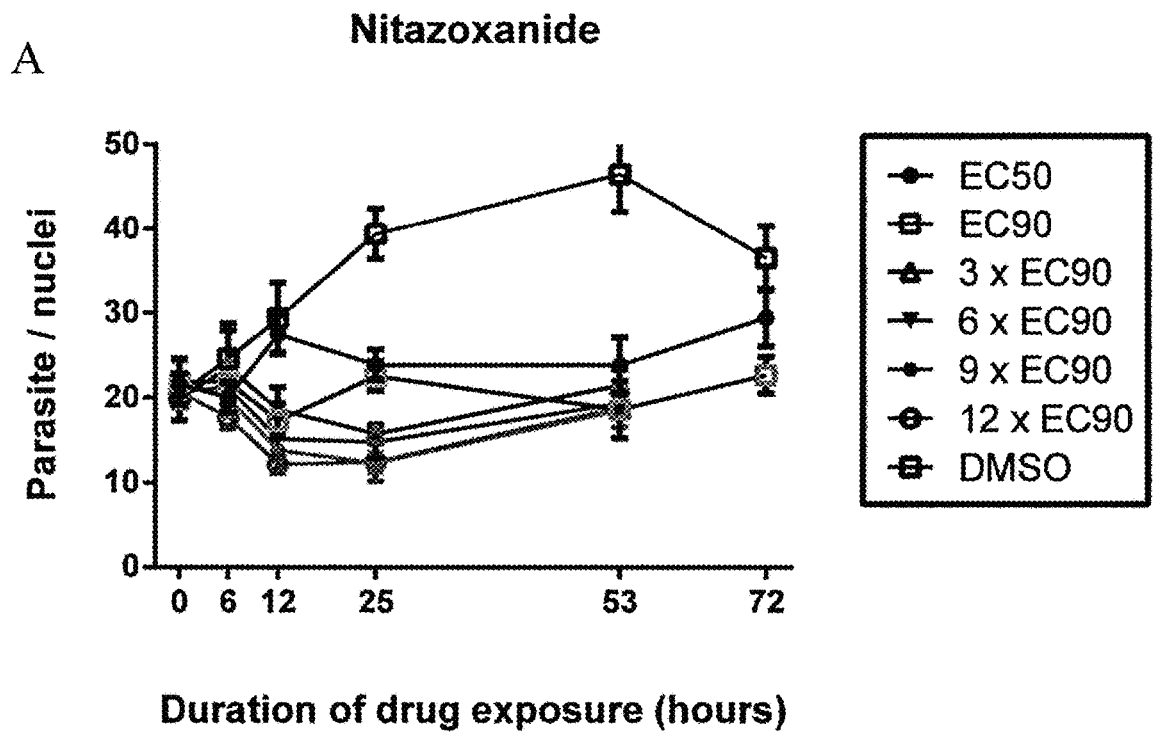
FIG. 7 shows the results of experiments to determine if MMV665917 or the current standard-of-care drug, nitazoxanide, are static or cidal against *C. parvum*, and the concentration of compound expressed as a multiple of the in vitro EC90 that is required to maximize the rate of parasite elimination. (A) Results for nitazoxanide, which appears to be static, since *C. parvum* persists indefinitely in the presence of concentrations up to 12× the EC90. (B) Results for MMV665917, which appears to be cidal for *C. parvum* at concentrations equal to or exceeding the EC90. The maximal rate of parasite elimination is achieved at compounds at concentrations at or exceeding 3×EC90. Furthermore, since additional increases in compound concentration have no effect on the rate of parasite elimination, it can be inferred that the mode-of-action of MMV665917 is time-dependent, rather than concentration dependent.
Figure 7:
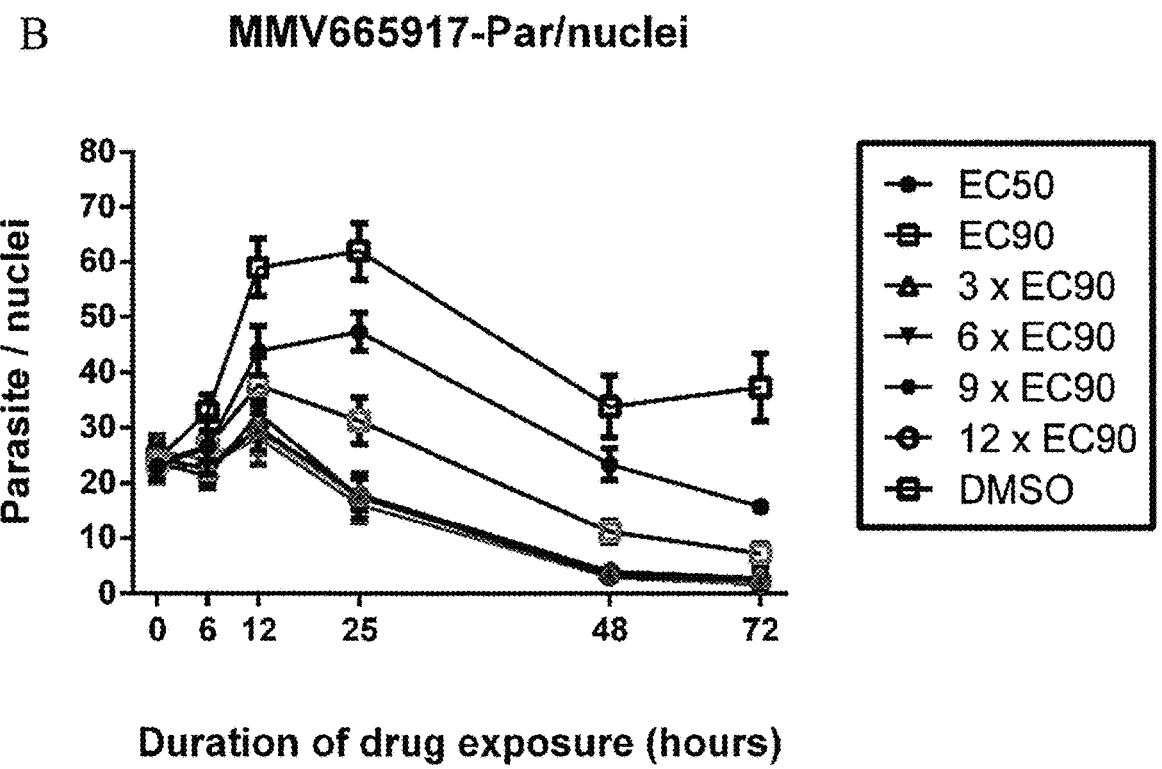

A repeat of the experiment presented in FIG. 2 showing efficacy of MMV665917 in the NOD SCID gamma mouse model is presented in FIG. 5. On repeat, 30 mg/kg twice daily was inactive, but 60 mg/kg twice daily eliminated detection of C. parvum shedding in the feces by real time PCR. Unlike the control compound paromomycin, no relapse was observed over the week following cessation of treatment. For this experiment, NOD SCID gamma mice were infected on day −6 by oral gavage of C. parvum oocysts, shedding was detected at day 0 prior to compound dosing, compounds or vehicle were dosed on days 0-6 as indicated, and mice were maintained for one week following cessation of treatment. Data shown are the mean and SE for the number of oocysts/mg stool detected by real time PCR of the feces on the indicated day (four mice per experimental group). The variable efficacy of MMV665917 dosed at 30 mg/kg twice daily is likely due to pharmacokinetic and pharmacodynamic factors detailed in FIGS. 6 through 9. In vitro data indicate that a compound concentration of greater than or equal to the EC90 concentration is required to achieve cidal anti-parasitic activity (i.e. parasite elimination), and that parasite elimination is time-dependent and thus requires sustained compound concentrations in excess of the EC90 concentration (see FIGS. 6 and 7). Based on measurement of serum compound concentrations and level modeling (see FIGS. 8 and 9), a twice daily dose of 60 mg/kg achieves concentrations in excess of the EC90 at all times, and reliable efficacy. On the other hand, the serum concentration exceeds the EC90 for just over ½ the dosing interval when MMV665917 is dosed at 30 mg/kg twice daily. This likely explains the variable efficacy of MMV665917 when given at this dose.

Figure 3:
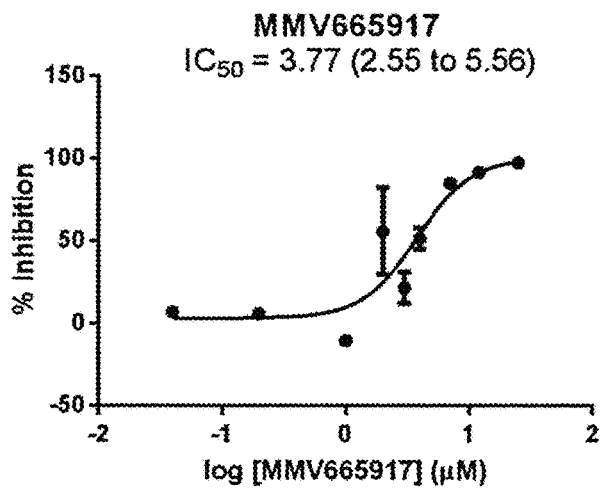
FIG. 3 shows an example of a representative dose response curve for MMV665917. The graph shows the relationship between an increasing concentration of MMV665917 and the corresponding inhibition of *C. parvum* in vitro.
Figure 3:
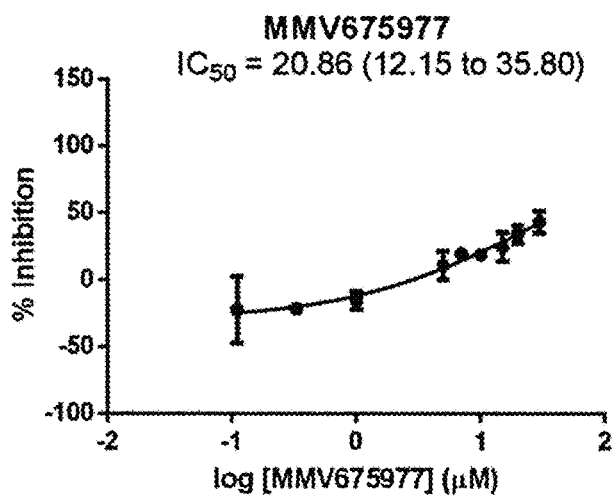
Figure 3:
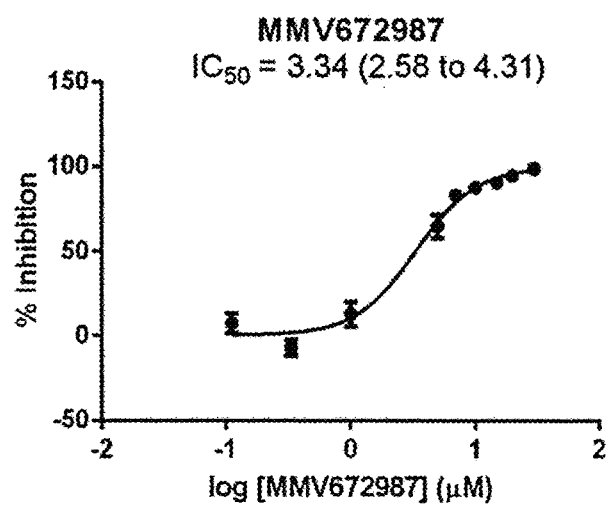

FIG. 3 shows results for in vitro dose-response curves with MMV665917 and the other MMV compounds tested in the NOD SCID gamma mouse model, as shown in FIG. 2. Results are combined data from two independent experiments, expressed as average percent inhibition and SD.

Conclusions. Based on its efficacy in the NOD SCID gamma immunocompromised mouse model, MMV665917 is a promising lead compound for treatment of cryptosporidiosis. The in vivo efficacy of MMV665917 is surprising and unexpected, given its in vitro potency. A number of compounds with greater in vitro potency and high systemic exposure following oral dosing in mice have no activity in the NOD SCID gamma mouse model.

Example 2

This example describes the evaluation of compounds of the present disclosure towards parasites.

To assess if MMV665917 is cidal or static for *C. parvum* and determine the concentration of compound required to maximize the rate of parasite elimination, *C. parvum* persistence in HCT-8 colonic carcinoma cells was assayed in the presence of increasing multiples of the in vitro EC90. The assay strategy and predictions are summarized in FIG. 6. Briefly, the assay infects HCT-8 intestinal epithelial cells with the *C. parvum* Iowa strain as in Example 1. Parasites are then allowed to develop for 24 hours prior to the addition of the indicated concentration of experimental compounds (time 0 in the graphs above). At the indicated times following compound addition, samples are then fixed, the host cells and parasites are fluorescently stained, and parasites are enumerated by automated epifluorescence microscopy and image process as described in Example 1.

FIG. 7A shows the results for the control compound nitazoxanide, which lacks activity in the NOD SCID gamma immunocompromised mouse model and in immunocompromised people. The compound appears to be static, since *C. parvum* persists indefinitely in the presence of as much as 12× the EC90 concentration. MMV665917 (FIG. 7B), on the other hand, appears to be cidal for *Cryptosporidium*, since parasites are eliminated at concentrations equal to or exceeding the $EC_{90}$. The maximal rate of parasite elimination is achieved at a compound concentration of 3×$EC_{90}$. Furthermore, since additional increases in the compound concentration have no effect on the rate of parasite elimination, the mode-of-action of MMV665917 appears to be time-dependent, rather than concentration dependent.

Example 3

This example details pharmacokinetic (PK) studies of a compound of the present disclosure.

The pharmacokinetics of MMV665917 were studied in overnight-fasted male Sprague Dawley rats that had access to water ad libitum throughout the pre- and post-dose sampling period, and access to food was re-instated 4 h (hour) post-dose.

MMV665917 was administered intravenously as a 10 min (minute) constant rate infusion via an indwelling jugular vein cannula (1 mL per rat, n=2 rats) and orally by gavage (10 mL/kg per rat, n=2 rats).

Samples of arterial blood and total urine were collected up to 24 h post-dose. Arterial blood was collected directly into borosilicate vials (at 4° C.) containing heparin, Complete® (a protease inhibitor cocktail), potassium fluoride, and EDTA to minimise potential for ex vivo degradation of test compound in blood/plasma samples. Once collected, blood samples were centrifuged, supernatant plasma was removed and stored frozen (−20° C.) until analysis by LC-MS.

Formulation Preparation and Analysis. Formulations were prepared on the day of dosing and animals were dosed within 45 minutes of preparation.

IV Formulation. MMV665917 was dissolved in propylene glycol and ethanol before Milli-Q water was added producing a clear solution. The formulation was filtered through a 0.22 μm syringe filter prior to dosing, and the measured concentration of compound the filtered solution was 0.24 mg/mL.

Oral Formulation. MMV665917 was wet milled in HPMC-SV in an agate mortar and sonicated for 10 minutes producing a uniform suspension. The bulk formulation was mixed by inverting the tubes prior to drawing each dosing volume and the average measured concentration of compound in aliquots (n=3) of formulation was 0.32 mg/mL (range 0.28-0.37 mg/mL).

In Vitro Determination of Plasma/Blood Stability and Whole Blood-to-Plasma Ratio. MMV665917 was spiked into fresh heparinized whole blood (collected from male Sprague Dawley rats) or plasma of a corresponding volume (which acted as a matrix control) to an initial nominal concentration of 500 ng/mL. As a whole blood assay for the compound was not available, the concentration of MMV665917 in the spiked plasma (i.e. matrix control) was used as a surrogate measurement of the spiked whole blood concentration. Whole blood samples were incubated at 37° C. for up to 240 min after which plasma and erythrocytes were separated by centrifugation prior to determination of plasma concentrations by LC-MS.

Whole blood-to-plasma partitioning ratios (B/P) were obtained by dividing the measured concentration in the plasma control sample by the concentration measured in plasma following centrifugation of whole blood.

Results and discussion. MMV665917 was stable in freshly collected rat plasma and whole blood when incubated in vitro at 37° C. (Table 2 in FIG. 4) suggesting that blood-mediated degradation not likely to contribute significantly to the in vivo clearance of the compound. The apparent in vitro whole blood to plasma partitioning ratio (B/P) of MMV665917 was 1.1.

No adverse reactions or compound related side effects were observed following IV or oral administration of MMV665917. Evidence of haemolysis was observed in plasma following IV administration, which can be attributed to the high organic content of the formulation vehicle (40% (v/v) propylene glycol and 10% (v/v) ethanol) which was required for solubilisation.

Plasma concentration versus time profiles of MMV665917 following IV and oral administration are presented in FIG. 1 and plasma concentrations from each rat are provided in Appendix 3. Pharmacokinetic parameters determined via non-compartmental analysis are summarized in Table 1 in FIG. 4.

Following IV administration, plasma concentrations remained above the analytical LLQ for 16 h and the apparent terminal half-life was approximately 3-4 h. The apparent volume of distribution was moderate and in vivo clearance was low. The fraction of the dose recovered in urine as intact MMV665917 over the 24 h sampling period was approximately 25%, suggesting that direct urinary excretion is a significant in vivo elimination route for this compound in rats.

Following oral administration, MMV665917 was slowly absorbed with maximum plasma concentrations being observed at 5 h post-dose and the apparent terminal half-life was consistent with that observed after IV dosing. The apparent oral bioavailability ranged from 24% to 43%. On the basis of the low in vivo blood clearance, it is likely that MMV665917 would be subject to low hepatic first pass elimination suggesting that oral exposure may be limited by solubility and/or permeability. Furthermore, given the consistency in the IV profiles, the approximately two-fold difference in oral exposure between rats may be indicative of variability in absorption-related processes. Further studies in a greater number of animals would be required to better define the basis for the observed variability.

FIG. 4 shows physical characteristics and mouse pharmacologic data for MMV665917. The compound shows moderate systemic exposure with slow intestinal absorption (i.e., the time to peak serum concentration following a single dose is 6 hours) and a prolonged serum half-life.

PK data for MMV665917 was also tested orally in rats. The compound exhibited an apparent terminal half-life of approximately 3-4 h, a moderate volume of distribution and low in vivo clearance. Following oral administration, the compound was slowly absorbed and apparent bioavailability was approximately 30%.

MMV665917 is absorbed from the intestine relatively slowly and incompletely, resulting in both prolonged intestinal exposure and systemic exposure. The unusual PK characteristics of MMV665917 may be a significant factor enabling in vivo efficacy.

Example 4

This example details additional pharmacokinetic studies of plasma concentration of MMV665917 on mice, rats and calves after administration.

Figure 8:
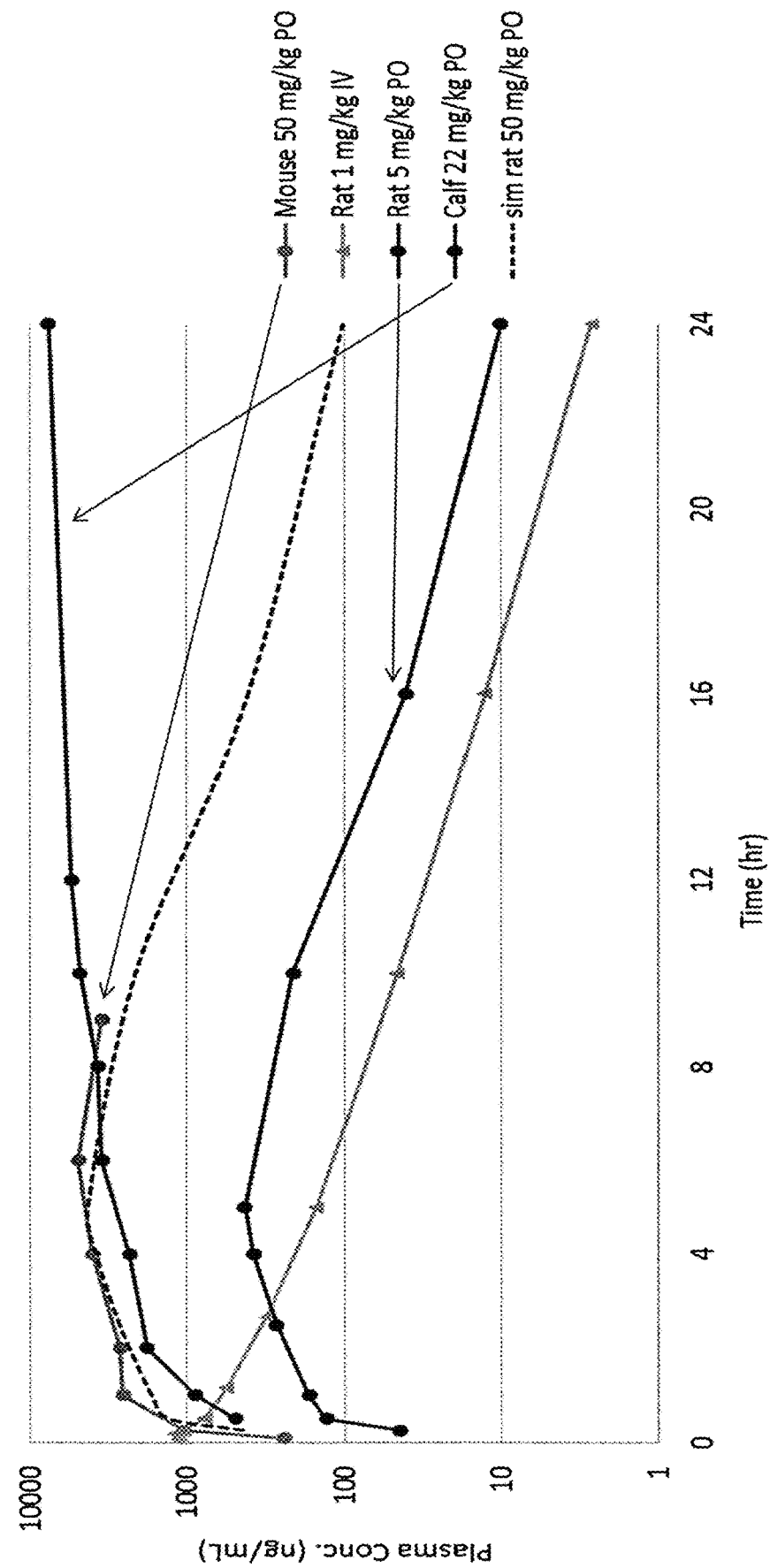
FIG. 8 shows the concentration of MMV665917 in mouse, rat and dairy calf plasma following administration of a single dose. Compounds were dosed as indicated either orally by oral gavage or intravenously, and serum samples were collected at the indicated time points. The MMV665917 plasma concentration was measured by LC-MS/MS. The dashed line shows the predicted plasma level out to 24 hours for mice, which was determined using the calculated elimination half-life.

The concentration of MMV665917 in mouse, rat and dairy calf plasma following a single dose is shown in FIG. 8. Compounds were dosed as indicated either orally by oral gavage or intravenously, and serum samples were collected at the indicated time points. The MMV665917 plasma concentration was measured by LC-MS/MS. The dashed line shows the predicted plasma level out to 24 hours for mice, which was determined using the calculated elimination half-life.

Figure 9:
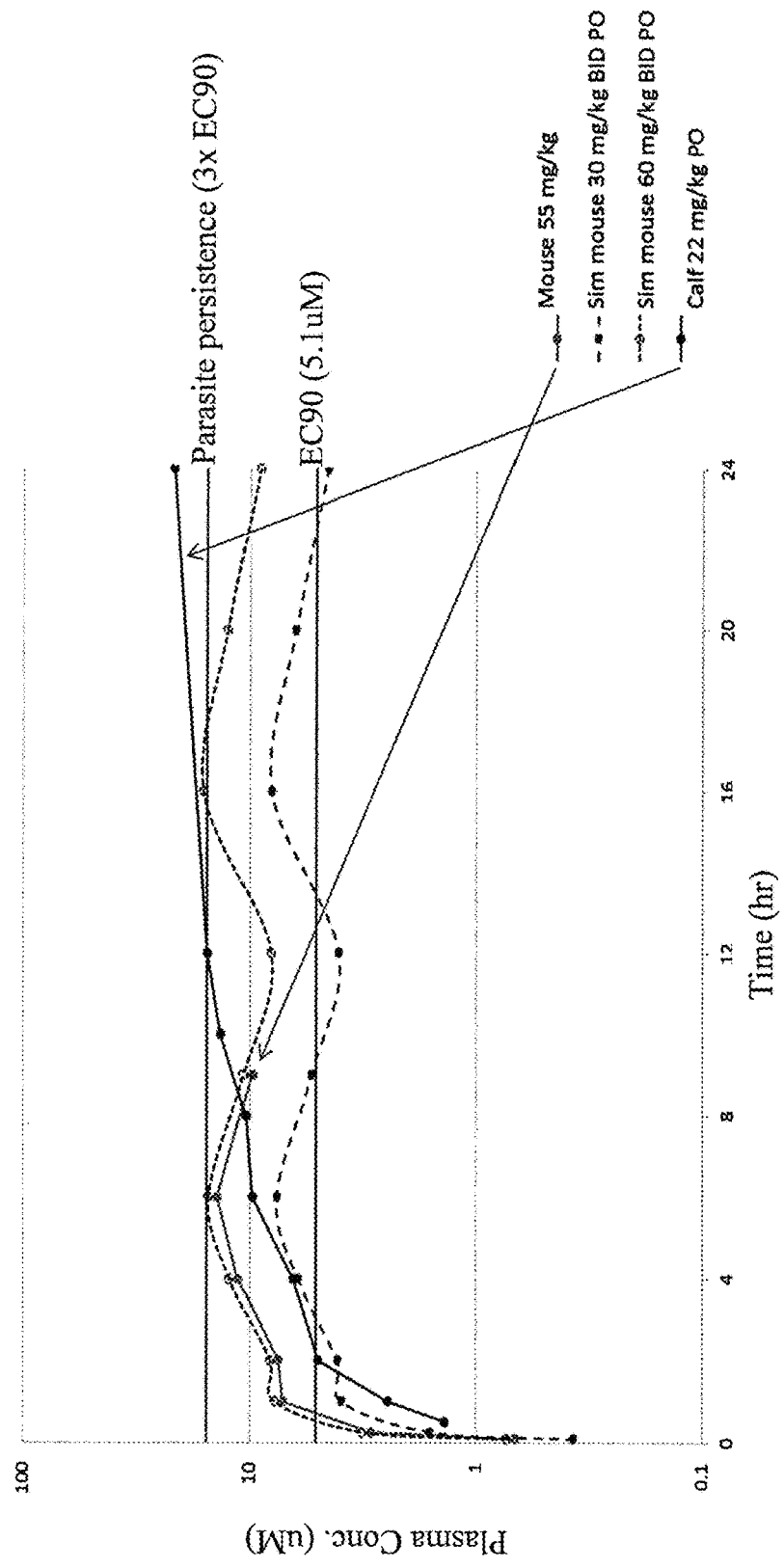
FIG. 9 shows the actual and simulated mouse and calf plasma concentrations for MMV665917, correlated to the EC90 and 3×EC90 concentrations. The data relate to those presented in FIGS. 5 and 7. Mouse serum concentrations measured from a single 55 mg/kg oral dose of MMV665917 (see above figure) were used to simulate the mouse serum concentrations following BID dosing of either 30 mg/kg or 60 mg/kg. The measured calf plasma concentration following a single 22 mg/kg oral dose is also shown. Note that a minimum concentration of EC90 was required for parasite elimination in vitro, and the rate of parasite elimination in vitro was maximized at 3× the EC90 concentration. Following 30 mg/kg BID dosing in mice, this concentration is not attained and MMV665917 was variably efficacious (i.e. effective in FIG. 2 and ineffective in the repeat experiment in FIG. 5). A 60 mg/kg BID dose, on the other hand, results in a sustained plasma concentration greater than the EC90, and is curative in the NOD SCID gamma mouse model (see FIG. 5).

The actual and simulated mouse and calf plasma concentrations for MMV665917, correlated to the EC90 and 3×EC90 concentrations are shown in FIG. 9. Mouse serum concentrations measured from a single 55 mg/kg oral dose of MMV665917 (FIG. 9) were used to simulate the mouse serum concentrations following BID dosing of either 30 mg/kg or 60 mg/kg. The measured calf plasma concentration following a single 22 mg/kg oral dose is also shown. Note that a minimum concentration of EC90 was required for parasite elimination in vitro, and the rate of parasite elimination in vitro was maximized at 3× the EC90 concentration. Following 30 mg/kg BID dosing in mice, this concentration is not attained and MMV665917 was variably efficacious. A 60 mg/kg BID dose, on the other hand, results in a sustained plasma concentration greater than the EC90, and is curative in the NOD SCID gamma mouse model.

Although the present disclosure has been described with respect to one or more particular embodiments and examples, it will be understood that other embodiments and examples of the present disclosure may be made without departing from the scope of the present disclosure.

What is claimed is:

1. A composition comprising a compound having the following structure:

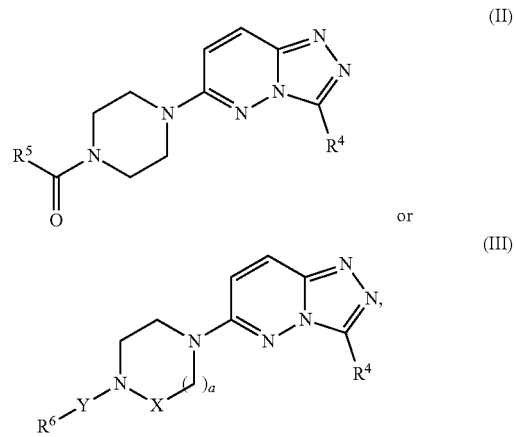

wherein $R^4$ is selected from the group consisting of hydrogen atom, substituted or unsubstituted $C_1$-$C_9$ alkyl groups, and haloalkyl groups;
$R^5$ is selected from the group consisting of substituted or unsubstituted benzyl groups, substituted or unsubstituted phenyl groups, substituted or unsubstituted phenoxy groups, and substituted or unsubstituted aniline groups;
$R^6$ is selected from the group consisting of substituted or unsubstituted $C_1$-$C_8$ alkyl groups, substituted or unsubstituted cycloalkyl groups, substituted or unsubstituted benzyl groups, substituted or unsubstituted phenyl groups, and substituted or unsubstituted heteroaryl groups;
Y is —$CH_2C(O)$—, wherein the —$CH_2$— of the —$CH_2C(O)$— group is covalently bonded to the asterisked nitrogen of the

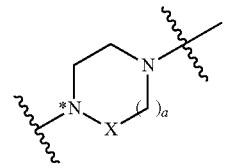

group of structure III;

X is —CH$_2$—; and a is 1, wherein the composition is for oral administration and the compound is encapsulated in a pH sensitive polymer suitable for release of the compound in the small intestines, distal small intestine, or colon and.

2. The composition of claim 1, wherein R$^5$ is selected from the group consisting of:

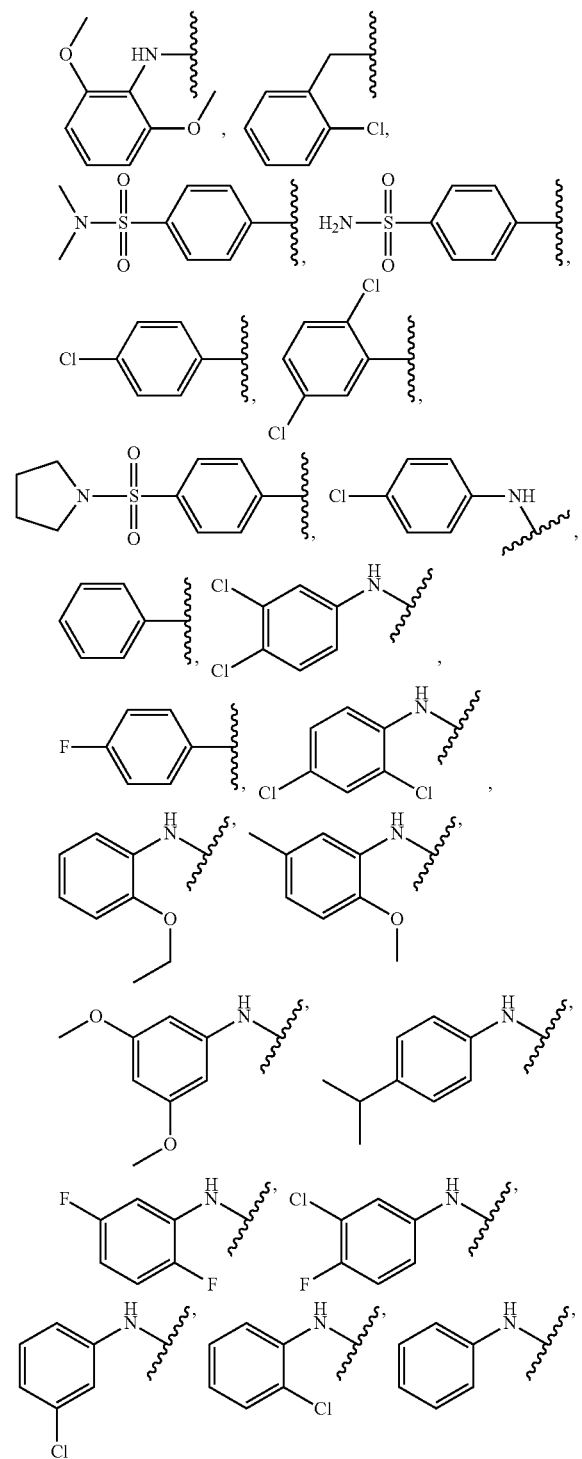

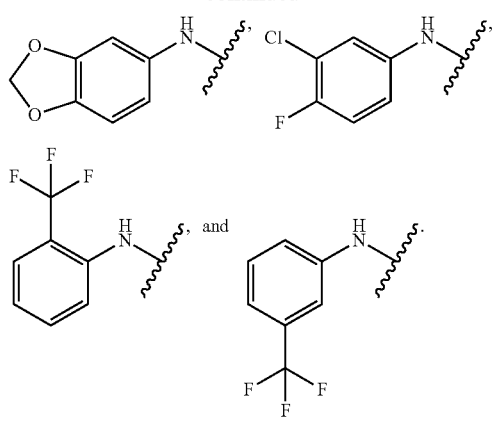

3. The composition of claim 1, wherein the compound is selected from the group consisting of:

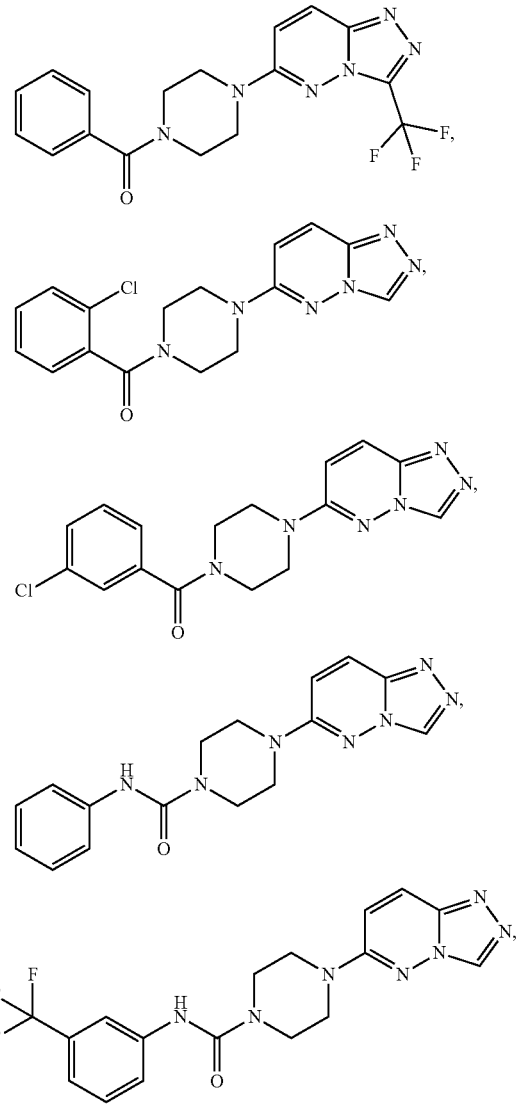

-continued
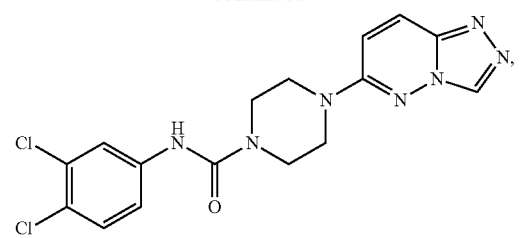
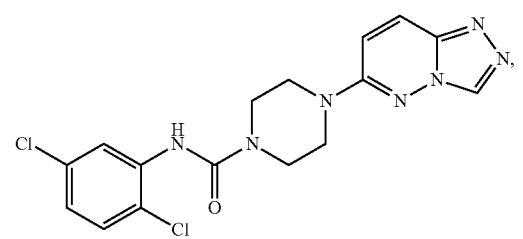
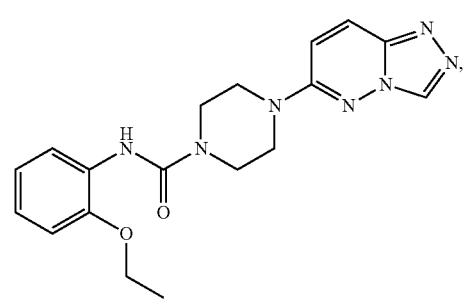
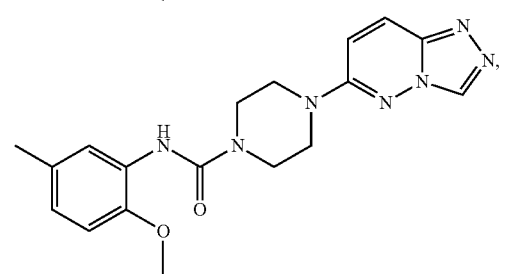
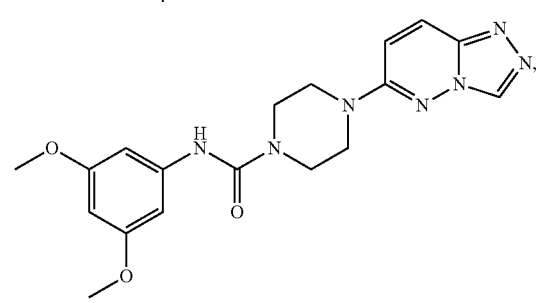
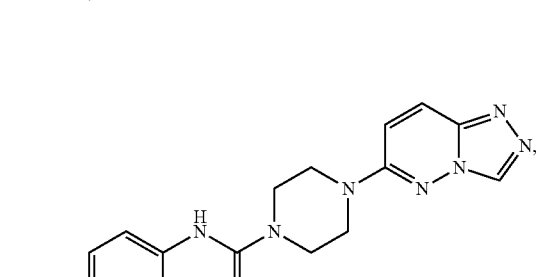
-continued
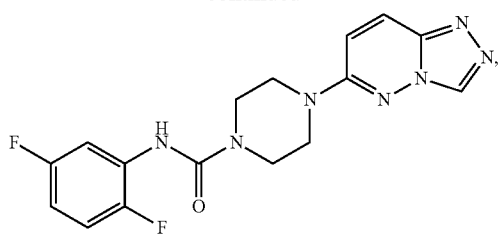
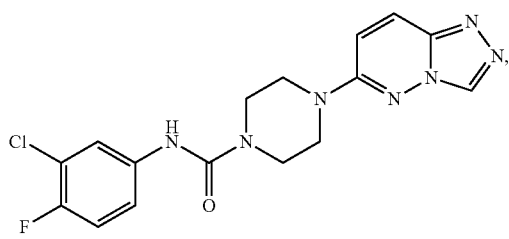
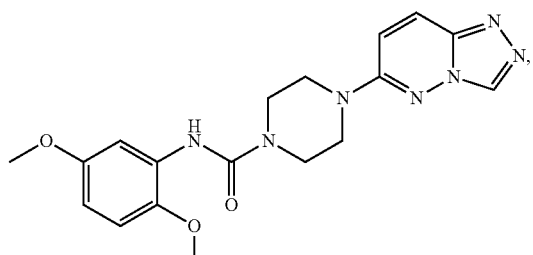
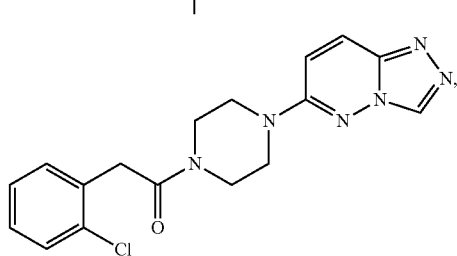
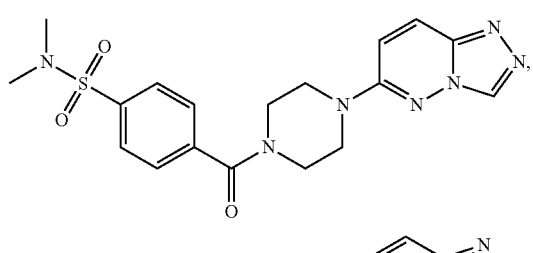
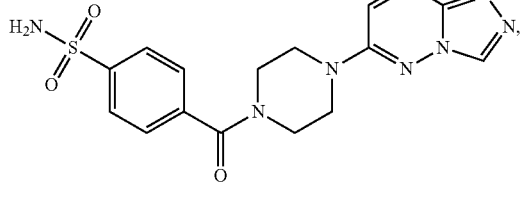
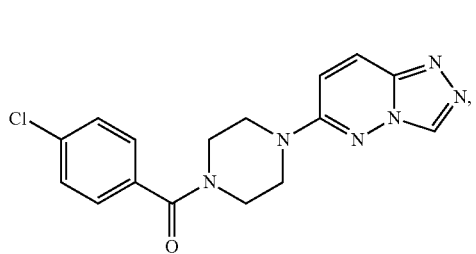

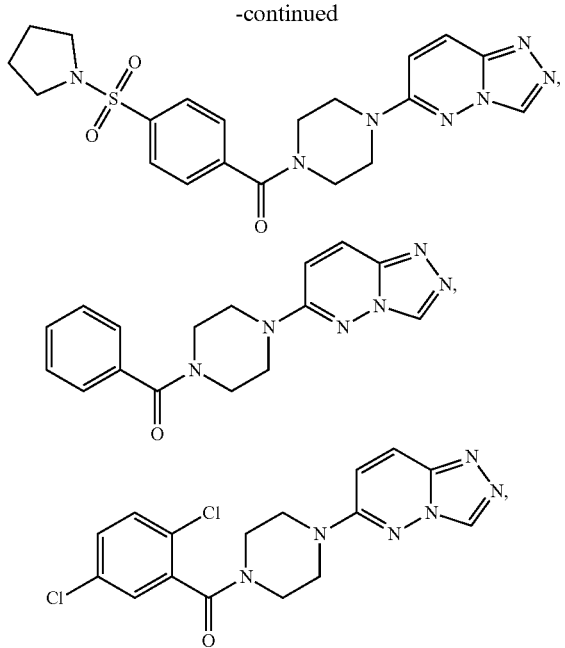
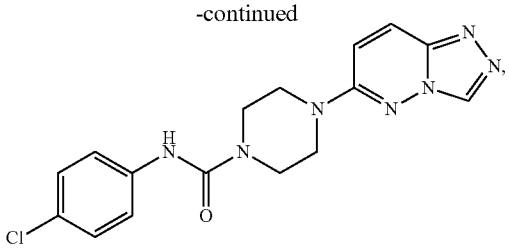
and combinations thereof.
4. A kit comprising a composition of claim 1 and instructions on administration details to an individual who has been diagnosed with or who is at risk of getting *cryptosporidium* infection wherein said details comprise one or more of the following: dosage, frequency, and length of time for administration of the composition.
* * * * *